US010316046B2

(12) United States Patent
Yamashita et al.

(10) Patent No.: US 10,316,046 B2
(45) Date of Patent: Jun. 11, 2019

(54) METHOD FOR PRODUCING ACYLOXYSILANES, ACYLOXYSILANES OBTAINED THEREBY, AND USE OF SAME

(71) Applicant: NATIONAL INSTITUTE OF ADVANCED INDUSTRIAL SCIENCE AND TECHNOLOGY, Tokyo (JP)

(72) Inventors: Hiroshi Yamashita, Ibaraki (JP); Makiko Hatori, Ibaraki (JP); Michiyo Yoshinaga, Ibaraki (JP); Li-Biao Han, Ibaraki (JP); Shigeru Shimada, Ibaraki (JP); Kazuhiko Sato, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 14 days.

(21) Appl. No.: 15/556,808

(22) PCT Filed: Mar. 9, 2016

(86) PCT No.: PCT/JP2016/057466
§ 371 (c)(1),
(2) Date: Sep. 8, 2017

(87) PCT Pub. No.: WO2016/143835
PCT Pub. Date: Sep. 15, 2016

(65) Prior Publication Data
US 2018/0044359 A1    Feb. 15, 2018

(30) Foreign Application Priority Data

Mar. 10, 2015    (JP) ................. 2015-046808

(51) Int. Cl.
C07F 7/18    (2006.01)
C07F 7/02    (2006.01)

(52) U.S. Cl.
CPC ............ C07F 7/1896 (2013.01); C07F 7/025 (2013.01); C07F 7/18 (2013.01)

(58) Field of Classification Search
None
See application file for complete search history.

(56) References Cited

U.S. PATENT DOCUMENTS

| 3,470,942 A * | 10/1969 | Hurutate ........... A23B 4/07 165/263 |
| 4,176,130 A | 11/1979 | John et al. |
| 4,379,766 A | 4/1983 | MacK et al. |
| 2003/0120010 A1 * | 6/2003 | Paul ............ C07F 7/1892 526/279 |
| 2011/0318681 A1 | 12/2011 | Osada et al. |

FOREIGN PATENT DOCUMENTS

| DE | 882401 C | 7/1953 | |
| EP | 0837067 B1 | 9/2002 | |
| JP | S49133331 A | 12/1974 | |
| JP | S5761052 A | 4/1982 | |
| JP | H03156468 A | 7/1991 | |
| JP | H04295486 A | * 10/1992 | ............... C07F 7/04 |
| JP | H04295486 A | 10/1992 | |
| JP | H0770152 A | 3/1995 | |
| JP | H10182666 A | 7/1998 | |

OTHER PUBLICATIONS

Machine Translation—Tsunemasa (JPH04295486A) (Year: 1992).*
Journal of the American Chemical Society, vol. 68 No. 11, pp. 2282-2284, Nov. 1946.
Journal of Organic Chemistry vol. V, pp. 443-448, 1940.
Effects and Use of Silane Coupling Agents, pp. 1-7, S&T Publishing, Inc., 2012.
International Search Report for PCT/JP2016/057466, dated Jun. 14, 2016.
International Preliminary Report on Patentability for PCT/JP2016/057466 dated Mar. 9, 2016.

* cited by examiner

Primary Examiner — Clinton A Brooks
Assistant Examiner — Kofi Adzamli
(74) Attorney, Agent, or Firm — Marshall, Gerstein & Borun LLP

(57) ABSTRACT

An object of the invention is to provide a method for efficiently producing an acyloxysilane which is useful as a functional chemical, an acyloxysilane obtained thereby, and the use thereof. The present invention provides: a method for producing an acyloxysilane, including a reaction step of reacting an alkoxysilane with a carboxylic anhydride in the presence of a catalyst, wherein the alkoxysilane is a specified alkoxysilane represented by General Formula (I), the carboxylic anhydride is a specified carboxylic acid represented by General Formula (IIA) or (IIB), the catalyst is an acid catalyst, and an acyloxysilane obtained in the reaction step is a specified acyloxysilane represented by General Formula (IIIA) or (IIIB); and the use of the acyloxysilane as a surface treatment agent or the like.

9 Claims, No Drawings

METHOD FOR PRODUCING ACYLOXYSILANES, ACYLOXYSILANES OBTAINED THEREBY, AND USE OF SAME

TECHNICAL FIELD

The present invention relates to a method for efficiently producing an acyloxysilane and the like, an acyloxysilane obtained thereby, and the use thereof.

BACKGROUND ART

Acyloxysilanes are functional chemicals which are used as reagents for precise synthesis and synthetic intermediates in pharmaceuticals, agricultural chemicals, electronic materials and the like, as well as raw materials for surface modifiers, sol/gel materials, nanomaterials, organic and inorganic hybrid materials, and the like.

As general methods for producing an acyloxysilane, the following methods are known, for example: (A) a method in which a chlorosilane is allowed to react with a carboxylic acid directly or in the presence of a base (Patent Documents 1 and 2); (B) a method in which a chlorosilane is allowed to react with a metal carboxylate (Patent Document 3); (C) a method in which an acyloxysilane is allowed to react with a carboxylic acid (Patent Document 4); (D) a method in which a hydrosilane is allowed to react with a carboxylic acid in the presence of a transition metal catalyst (Patent Document 5); (E) a method in which a chlorosilane is allowed to react with a carboxylic anhydride (Patent Document 6); (F) a method in which silanol is allowed to react with a carboxylic anhydride (Non-patent Document 1); and (G) a method in which an alkoxysilane is allowed to react with a carboxylic anhydride (Non-patent Document 2).

However, the methods using a chlorosilane are associated with the following problems: (1) handling of raw materials is not easy, since a chlorosilane, which generates corrosive hydrogen chloride due to hydrolysis, is used (methods A and B); (2) corrosive hydrogen chloride is produced as a byproduct, in cases where a base is not used in the reaction with a carboxylic acid (method A); (3) a large amount of salt is produced as a byproduct, in cases where a base is used in the reaction with a carboxylic acid (method A); (4) a large amount of salt is produced as a byproduct, also in the reaction with a metal carboxylate (method B); (5) an acyl chloride, which is susceptible to hydrolysis and prone to generate corrosive hydrogen chloride, is produced as a byproduct, in the reaction with a carboxylic anhydride (method E); and the like. Further, the method using an acyloxysilane, a hydrosilane, or silanol (method C, D or F) is associated with a problem that such a silicon compound or the like is not necessarily easily available, is expensive, or the like. In addition, the method using an alkoxysilane (method G) has a problem that a mixture of raw materials needs to be heated at a high reflux temperature for a prolonged period of time, and thus, a more industrially advantageous approach has been demanded.

On the other hand, regarding the applications of acyloxysilanes or related silicon compounds, a method has been known, as one of the methods for carrying out a surface treatment of a solid material, in which a trialkoxysilane such as triethoxysilane or trimethoxysilane, or triacetoxysilane or the like having a higher reactivity, is used as a so-called silane coupling agent (Non-patent Document 3).

However, the method using a trialkoxysilane has the following problems: the operational process is not simple, since a trialkoxysilane is less likely to react directly with the surface of a solid material, and thus it is necessary, in general, to convert it into the structure of silanol by carrying out the hydrolysis of alkoxy groups in the presence of water; the efficiency of the surface treatment is not necessarily high, because a coupling reaction of silanols simultaneously proceeds along with the reaction with the solid material surface; and the like. In contrast, the method using triacetoxysilane is associated with problems such as, for example, that easily obtainable, commercially available types of triacetoxysilane are limited to specific types. The reason for this is as follows: although triacetoxysilane has a high reactivity with a solid material surface, the use thereof in a conventional method results in an increased production cost; triacetoxysilane is unstable to moisture or water, and has a low storage stability; or the like.

PRIOR ART DOCUMENTS

Patent Documents

Patent Document 1: JP 54-103500 A
Patent Document 2: European Patent No. 0837067
Patent Document 3: U.S. Pat. No. 4,379,766
Patent Document 4: JP 7-70152 A
Patent Document 5: JP 10-182666 A
Patent Document 6: German Patent No. 882401

Non-Patent Documents

Non-patent Document 1: J. Am. Chem. Soc., 68, 2282-2284 (1946)
Non-patent Document 2: J. Org. Chem., 5, 443-448 (1940)
Non-patent Document 3: Effects and Use of Silane Coupling Agents, complete revised version, Chapter One, S&T Publishing (2012)

SUMMARY OF THE INVENTION

Problems to be Solved by the Invention

The present invention has been made in view of the above mentioned problems, and an object of the present invention is to provide a method for more efficiently producing an acyloxysilane, a novel acyloxysilane obtained thereby, and the use thereof.

Means for Solving the Problems

As a result of intensive studies to solve the above mentioned problems, the present inventors have discovered that it is possible to allow the reaction of an easily available alkoxysilane with a carboxylic anhydride to proceed smoothly in the presence of a specific catalyst, and thus to efficiently obtain an acyloxysilane, and that the resulting acyloxysilane can be used as a surface treatment agent for treating a solid material, or the like, thereby completing the present invention.

In other words, this application provides the following inventions.

<1> A method for producing an acyloxysilane, including a reaction step of reacting an alkoxysilane with a carboxylic anhydride in the presence of a catalyst, wherein the alkoxysilane is an alkoxysilane represented by the following General Formula (I), the carboxylic anhydride is a carboxylic anhydride represented by the following General Formula (IIA) or (IIB),
the catalyst is an acid catalyst, and
an acyloxysilane obtained in the reaction step is an acyloxysilane represented by the following General Formula (IIIA) or (IIIB):

$$R^1_p R^2_q R^3_r Si(OR^4)_{4-(p+q+r)} \quad (I)$$

wherein p, q, r, and the sum of p+q+r are each an integer of 0 or more and 3 or less; each of $R^1$, $R^2$ and $R^3$ independently represents a hydrocarbon group having from 1 to 24 carbon atoms or a hydrogen atom; $R^4$(s) is/are an alkyl group(s) having from 1 to 6 carbon atoms; and in cases where each of $R^1$, $R^2$, and $R^3$ is a hydrocarbon group, some of the hydrogen atoms of the hydrocarbon group is/are optionally substituted with a group(s) not participating in the reaction;

$$(R^5CO)_2O \quad (IIA)$$

wherein each $R^5$ is a hydrocarbon group having from 1 to 24 carbon atoms, and some of the hydrogen atoms of the hydrocarbon group is/are optionally substituted with a group(s) not participating in the reaction;

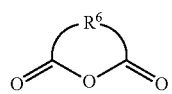
(IIB)

wherein $R^6$ is a divalent hydrocarbon group having from 2 to 24 carbon atoms, and some of the hydrogen atoms of the hydrocarbon group is/are optionally substituted with a group(s) not participating in the reaction;

$$R^1_p R^2_q R^3_r Si(OR^4)_{4-(p+q+r+s)}(OCOR^5)_s \quad (IIIA)$$

wherein p, q, r, $R^1$, $R^2$, $R^3$, $R^4$ and $R^5$ are each the same as defined above;
and s is an integer equal to or greater than 1 and equal to or less than 4−(p+q+r);

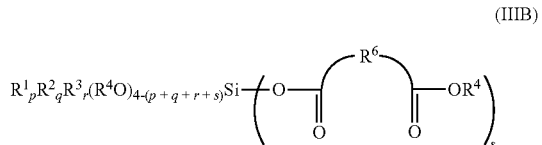
(IIIB)

wherein p, q, r, $R^1$, $R^2$, $R^3$, $R^4$ and $R^6$ are each the same as defined above; and s is an integer equal to or greater than 1 and equal to or less than 4−(p+q+r).

<2> The method for producing an acyloxysilane according to <1>, wherein the acid catalyst is an inorganic or organic acid.

<3> The method for producing an acyloxysilane according to <2>, wherein the inorganic acid is an inorganic solid acid having a regular pore structure and/or a layered structure.

<4> The method for producing an acyloxysilane according to <3>, wherein the inorganic solid acid is a zeolite and/or a montmorillonite.

<5> The method for producing an acyloxysilane according to <4>, wherein the zeolite has a silica/alumina ratio (amount of substance ratio) of from 3 to 1,000.

<6> The method for producing an acyloxysilane according to <4> or <5>, wherein the zeolite is at least one selected from the group consisting of USY-type zeolites, beta-type zeolites, Y-type zeolites, ZSM-5-type zeolites and mordenite-type zeolites.

<7> The method for producing an acyloxysilane according to <2>, wherein the inorganic acid is a chloride, a bromide or a perchlorate containing an element selected from iron, ruthenium, aluminum, scandium, tin or indium.

<8> The method for producing an acyloxysilane according to <2>, wherein the inorganic or organic acid is a sulfonic acid, a sulfonylimide, or a salt formed from any of these acids and an element selected from iron, ruthenium, aluminum, scandium, tin or indium.

<9> The method for producing an acyloxysilane according to any one of <1> to <8>, wherein the reaction step is carried out under microwave irradiation.

<10> An acyloxysilane represented by the following General Formula (IIIC) or (IIID):

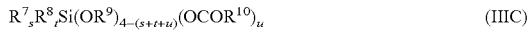
$$R^7_s R^8_t Si(OR^9)_{4-(s+t+u)}(OCOR^{10})_u \quad (IIIC)$$

wherein each of $R^7$, $R^8$, $R^9$ and $R^{10}$ independently represents a hydrocarbon group having from 1 to 12 carbon atoms, or a hydrocarbon group which has from 1 to 12 carbon atoms and in which some of the hydrogen atoms is/are substituted with a halogen atom(s), and at least one of the hydrocarbon groups represented by $R^7$, $R^8$, $R^9$ and $R^{10}$ has three or more carbon atoms, is an alkenyl group, or contains a halogen atom; s, t, and the sum of s+t are each an integer of 0 or more and 2 or less; and u and the value of 4−(s+t+u) are each an integer of 1 or more and 3 or less.

<11> A surface treatment agent including an acyloxysilane produced by the method according to any one of <1> to <9>.

<12> A surface treatment agent including an acyloxysilane represented by the General Formula (IIIC) or (IIID) recited in <10>.

<13> A method for performing a surface treatment of a solid material, using the surface treatment agent according to <11> or <12>.

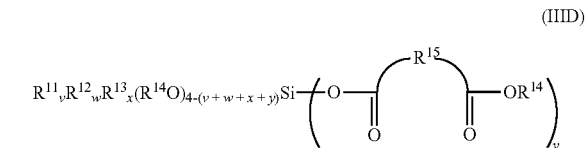
(IIID)

wherein each of $R^{11}$, $R^{12}$, $R^{13}$ and $R^{14}$ independently represents a hydrocarbon group having from 1 to 12 carbon atoms; $R^{15}$(s) is/are a divalent hydrocarbon group(s) having from 2 to 8 carbon atoms; v, w, x, and the sum of v+w+x are each an integer of 0 or more and 3 or less; and y is an integer equal to or greater than 1 and equal to or less than 4−(v+w+x).

Effect of the Invention

The method for producing an acyloxysilane according to the present invention allows for a more efficient production of an acyloxysilane as compared to conventional methods, as well as providing a novel acyloxysilane.

Specifically, the production method according to the present invention has the following characteristics.

(1) The raw materials and the catalyst to be used are easily available, easily handleable, and highly safe.

(2) The separation, collection and the like of the catalyst can be performed easily, in a reaction system which utilizes a solid catalyst.

(3) Some or all of a plurality of alkoxy groups can be selectively converted into an acyloxy group(s), by controlling the reaction conditions.

(4) It is possible to produce an acyloxysilane having an alkoxycarbonyl group at a terminal of its acyloxy group, by using a cyclic carboxylic anhydride.

(5) Microwave irradiation can be used to enhance the reaction.

(6) It is possible to provide a novel acyloxysilane by the production method according to the present invention.

The production method according to the present invention allows for a reduction in the cost and an improvement in the efficiency of the production process, and thus is considered to have significant advantages in terms of economic efficiency, environmental stress and the like, as compared to conventional techniques.

EMBODIMENTS FOR CARRYING OUT THE INVENTION

The present invention will now be described in detail.

The production method according to the present invention is characterized by including a reaction step of reacting an alkoxysilane with a carboxylic anhydride in the presence of a catalyst.

In the present invention, an alkoxysilane to be used as a raw material, namely, a starting alkoxysilane to be used in the reaction, is represented by the following General Formula (I):

In General Formula (I), p, q, r, and the sum of p+q+r are each an integer of 0 or more and 3 or less. Further, each of $R^1$, $R^2$ and $R^3$ independently represents a hydrocarbon group having from 1 to 24 carbon atoms or a hydrogen atom; and $R^4$(s) is/are an alkyl group(s) having from 1 to 6 carbon atoms. In cases where each of $R^1$, $R^2$, and $R^3$ is a hydrocarbon group, some of the hydrogen atoms of the hydrocarbon group is/are optionally substituted with a group(s) not participating in the reaction.

Specific examples of the hydrocarbon group include alkyl groups, aryl groups, aralkyl groups, and alkenyl groups.

In cases where the hydrocarbon group is an alkyl group, the alkyl group preferably has from 1 to 20 carbon atoms, more preferably from 1 to 18 carbon atoms, and some or all of the hydrogen atoms on carbon atoms are optionally substituted with a group(s) not participating in the reaction. Specific examples of the group not participating in the reaction include: alkoxy groups having from 1 to 6 carbon atoms, alkoxycarbonyl groups having from 1 to 6 carbon atoms, dialkylamino groups having from 1 to 6 carbon atoms, cyano group, nitro group, and halogen atoms. More specific examples of the alkoxy groups, alkoxycarbonyl groups, dialkylamino groups, and halogen atoms include: alkoxy groups such as methoxy group, ethoxy group and hexoxy group; alkoxycarbonyl groups such as methoxycarbonyl group and propoxycarbonyl group; dialkylamino groups such as dimethylamino group and diethylamino group; and halogen atoms such as fluorine atom, chlorine atom, and bromine atom. Specific examples of the alkyl group having any of these groups and the like include: methyl group, ethyl group, propyl group, butyl group, sec-butyl group, pentyl group, hexyl group, cyclohexyl group, octyl group, decyl group, 2-methoxyethyl group, 3-ethoxy-propyl group, 2-methoxycarbonylethyl group, 2-dimethyl-aminoethyl group, 2-cyanoethyl group, trifluoromethyl group, 3-chloropropyl group, 3,3,3-trifluoropropyl group, 1H,1H,2H,2H-tridecafluorooctyl group, and 1H,1H,2H,2H-heptadecafluorodecyl group.

Further, in cases where the hydrocarbon group is an aryl group, a monovalent aromatic organic group of a hydrocarbon ring system or a heterocyclic ring system can be used. When the aryl group is a monovalent aromatic organic group of a hydrocarbon ring system, the aryl group preferably has from 6 to 22 carbon atoms, and more preferably from 6 to 14 carbon atoms. Specific examples of such an aryl group include phenyl group, naphthyl group, anthryl group, phenanthryl group, pyrenyl group, perylenyl group, and pentacenyl group. Further, when the aryl group is a monovalent aromatic organic group of a heterocyclic ring system, the heterocyclic ring contains a hetero atom such as a sulfur atom or an oxygen atom, and the aryl group preferably has from 4 to 12 carbon atoms, and more preferably from 4 to 8 carbon atoms. Specific examples of such an aryl group include thienyl group, benzothienyl group, dibenzothienyl group, furyl group, benzofuryl group, and dibenzofuryl group. Some of the hydrogen atoms of the aryl group is/are optionally substituted with a group(s) not participating in the reaction. Specific examples of the group not participating in the reaction include those described above for the case where the hydrocarbon group is an alkyl group. In addition, examples of the group not participating in the reaction, other than those mentioned above, include oxyethylene group and oxyethyleneoxy group, each of which is a divalent group that links two carbon atoms on the ring. Specific examples of the aryl group having any of these groups and the like include methylphenyl group, ethylphenyl group, hexylphenyl group, methoxyphenyl group, ethoxyphenyl group, butoxy phenyl group, octoxyphenyl group, methyl (methoxy)phenyl group, fluoro(methyl)phenyl group, chloro (methoxy)phenyl group, bromo(methoxy)phenyl group, 2,3-dihydrobenzofuranyl group, and 1,4-benzodioxanyl group.

Further, in cases where the hydrocarbon group is an aralkyl group, the aralkyl group preferably has from 7 to 23 carbon atoms, more preferably from 7 to 16 carbon atoms, and some or all of the hydrogen atoms on carbon atoms are optionally substituted with a group(s) not participating in the reaction.

Specific examples of the group not participating in the reaction include those described above for the case where the hydrocarbon group is an alkyl group.

Specific examples of the aralkyl group having any of these groups and the like include benzyl group, phenethyl group, 2-naphthylmethyl group, 9-anthrylmethyl group, (4-chlorophenyl)methyl group, and 1-(4-methoxyphenyl) ethyl group.

Further, in cases where the hydrocarbon group is an alkenyl group, the alkenyl group preferably has from 2 to 23 carbon atoms, more preferably from 2 to 20 carbon atoms, and some or all of the hydrogen atoms on carbon atoms are optionally substituted with a group(s) not participating in the reaction.

Specific examples of the group not participating in the reaction include those described above for the case where the hydrocarbon group is an alkyl group, as well as those described above for the case where the hydrocarbon group is an aryl group.

Specific examples of the alkenyl group having any of these groups and the like include vinyl group, 2-propenyl group, 3-butenyl group, 5-hexenyl group, 9-decenyl group, 2-phenylethenyl group, 2-(methoxyphenyl)ethenyl group, 2-naphthylethenyl group, and 2-anthrylethenyl group.

Accordingly, specific examples of the starting alkoxysilane having any of the above described hydrocarbon groups and the like include trimethyl(methoxy)silane, trimethyl(ethoxy)silane, methylphenyldi(methoxy)silane, dimethyldi(methoxy)silane, dimethyldi(ethoxy)silane, di(ethoxy)(phenyl)vinylsilane, methyltri(methoxy)silane, methyltri(ethoxy)silane, phenyltri(methoxy)silane, phenyltri(ethoxy)silane, vinyltri(methoxy)silane, vinyltri(ethoxy)silane, tri(methoxy)silane, tri(ethoxy)silane, tetra(methoxy)silane, tetra(ethoxy)silane, tetra(propoxy)silane, and tetra(butoxy)silane.

On the other hand, a carboxylic anhydride to be reacted with any of the above described alkoxysilanes is represented by the following General Formula (IIA):

$$(R^5CO)_2O \quad \text{(IIA)},$$

or the following General Formula (IIB).

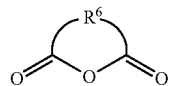

(IIB)

In General Formula (IIA), each $R^5$ is a hydrocarbon group having from 1 to 24 carbon atoms, and some of the hydrogen atoms of the hydrocarbon group is/are optionally substituted with a group(s) not participating in the reaction. Specific examples of the hydrocarbon group as described above include alkyl groups, aryl groups, aralkyl groups, and alkenyl groups. Specific examples of the group not participating in the reaction include those mentioned above in the description of $R^1$, $R^2$ or $R^3$ in the above described General Formula (I).

The number of carbon atoms in the hydrocarbon group is: preferably from 1 to 20, and more preferably from 1 to 18, in cases where the hydrocarbon group is an alkyl group; preferably from 4 to 20, and more preferably from 4 to 18, in the case of an aryl group; preferably from 5 to 21, and more preferably from 5 to 19, in the case of an aralkyl group; and preferably from 2 to 20, and more preferably from 2 to 18, in the case of an alkenyl group.

Specific examples of these hydrocarbon groups include those mentioned above in the description of $R^1$, $R^2$ or $R^3$ in the above described General Formula (I).

Accordingly, specific examples of the carboxylic anhydride of General Formula (IIA) having any of the above described hydrocarbon groups include acetic anhydride, propionic anhydride, butyric anhydride, isobutyric anhydride, valeric anhydride, isovaleric anhydride, pivalic anhydride, hexanoic anhydride, heptanoic anhydride, cyclohexanecarboxylic anhydride, octanoic anhydride, nonanoic anhydride, decanoic anhydride, lauric anhydride, myristic anhydride, palmitic anhydride, stearic anhydride, difluoroacetic anhydride, trifluoroacetic anhydride, trichloroacetic anhydride, chlorodifluoroacetic anhydride, benzoic anhydride, toluic anhydride, naphthoic anhydride, phenyl acetic anhydride, crotonic anhydride, isocrotonic anhydride, tiglic anhydride, and oleic anhydride.

Further, in General Formula (IIB), $R^6$ is a divalent hydrocarbon group having from 2 to 24 carbon atoms, and some of the hydrogen atoms of the hydrocarbon group is/are optionally substituted with a group(s) not participating in the reaction.

Specific examples of the divalent hydrocarbon group include alkylene groups, arylene groups, and alkenylene groups. Specific examples of the group not participating in the reaction include those mentioned above in the description of $R^1$, $R^2$ or $R^3$ in the above described General Formula (I).

The number of carbon atoms in the divalent hydrocarbon group is: preferably from 1 to 20, and more preferably from 1 to 18, in cases where the divalent hydrocarbon group is an alkylene group; preferably from 4 to 20, and more preferably from 4 to 18, in the case of an arylene group; and preferably from 2 to 20, and more preferably from 2 to 18, in the case of an alkenylene group.

Specific examples of these hydrocarbon groups include ethylene group, trimethylene group, tetramethylene group, pentamethylene group, hexamethylene group, cyclohexane-1,2-diylgroup, 4-methylcyclo-1,2-diylgroup, 1,2-phenylene group, 4-methyl-1,2-phenylene group, 4-bromo-1,2-phenylene group, vinylene group, and 2-methylpropenylene group.

Accordingly, specific examples of the carboxylic anhydride of General Formula (IIB) having any of the above described hydrocarbon groups and the like include succinic anhydride, octyl succinic anhydride, 2,2-dimethylsuccinic anhydride, glutaric anhydride, 3-methylglutaric anhydride, cyclohexane-1,2-dicarboxylic anhydride, 4-methylcyclohexane-1,2-dicarboxylic anhydride, phthalic anhydride, 4-methylphthalic anhydride, 4-bromophthalic anhydride, 4-nitrophthalic anhydride, biphenyl-2,2'-dicarboxylic anhydride, naphthalene-1,8-dicarboxylic anhydride, maleic anhydride, itaconic anhydride, and 5-norbornene-2,3-dicarboxylic anhydride.

The molar ratio of the carboxylic anhydride to the starting alkoxysilane can be selected arbitrarily. However, the molar ratio is usually from 0.4 to 300, more preferably from 0.5 to 200, and still more preferably from 0.5 to 150, in terms of the yield of the resulting acyloxysilane with respect to the starting alkoxysilane.

According to the present invention, by allowing the alkoxysilane represented by the above described General Formula (I) to react with the carboxylic anhydride represented by the above described General Formula (IIA) or (IIB), it is possible to obtain, respectively, an acyloxysilane represented by the following General Formula (IIIA):

$$R^1_pR^2_qR^3_rSi(OR^4)_{4-(p+q+r+s)}(OCOR^5)_s \quad \text{(IIIA)}$$

or an acyloxysilane represented by the following General Formula (IIIB).

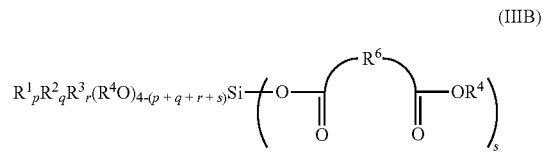

(IIIB)

In General Formulae (IIIA) and (IIIB), p, q, r, $R^1$, $R^2$, $R^3$, $R^4$, $R^5$ and $R^6$ are each the same as defined above, and specific examples thereof include those mentioned in the descriptions of the above described General Formulae (I) (IIA) and (IIB). In addition, s is an integer equal to or greater than 1 and equal to or less than 4−(p+q+r).

Further, the production method according to the present invention allows for providing acyloxysilanes represented by the following General Formulae (IIIC) and (IIID).

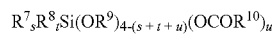 (IIIC)

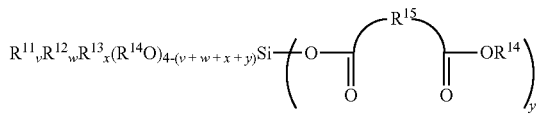 (IIID)

In General Formula (IIIC), each of $R^7$, $R^8$, $R^9$ and $R^{10}$ independently represents a hydrocarbon group having from 1 to 12 carbon atoms, or a hydrocarbon group which has from 1 to 12 carbon atoms and in which some of the hydrogen atoms is/are substituted with a halogen atom(s); and at least one of the hydrocarbon groups represented by $R^7$, $R^8$, $R^9$ and $R^{10}$ has three or more carbon atoms, is an alkenyl group, or contains a halogen atom. Further, s, t, and the sum of s+t are each an integer of 0 or more and 2 or less; and u and the value of 4−(s+t+u) are each an integer of 1 or more and 3 or less.

In General Formula (IIID), each of $R^{11}$, $R^{12}$, $R^{13}$ and $R^{14}$ independently represents a hydrocarbon group having from 1 to 12 carbon atoms; $R^{15}$(s) is/are a divalent hydrocarbon group(s) having from 2 to 8 carbon atoms; v, w, x, and the sum of v+w+x are each an integer of 0 or more and 3 or less; and y is an integer equal to or greater than 1 and equal to or less than 4−(v+w+x).

Examples of the hydrocarbon group having from 1 to 12 carbon atoms, in General Formula (IIIC) and General Formula (IIID), include alkyl groups, aryl groups, aralkyl groups, and alkenyl groups. Specific examples thereof include methyl group, ethyl group, propyl group, butyl group, pentyl group, hexyl group, octyl group, decyl group, dodecyl group, phenyl group, benzyl group, vinyl group, and allyl group. Examples of the hydrocarbon group which has from 1 to 12 carbon atoms and in which some of the hydrogen atoms is/are substituted with a halogen atom(s), in General Formula (IIIC), include chloromethyl group, dichloromethyl group, trichloromethyl group, chlorodifluoromethyl group, pentafluorophenyl group, 3,3,3-trifluoropropyl group, 1H,1H,2H,2H-tridecafluorooctyl group, and 1H,1H,2H,2H-heptadecafluorodecyl group.

Further, specific examples of the at least one of the hydrocarbon groups represented by $R^7$, $R^8$, $R^9$ and $R^{10}$ in General Formula (IIIC), which hydrocarbon group has three or more carbon atoms, is an alkenyl group, or contains a halogen atom, include propyl group, butyl group, phenyl group, vinyl group, allyl group, chloromethyl group, dichloromethyl group, trichloromethyl group, chlorodifluoromethyl group, pentafluorophenyl group, 3,3,3-trifluoropropyl group, 1H,1H,2H,2H-tridecafluorooctyl group, and 1H,1H,2H,2H-heptadecafluorodecyl group.

On the other hand, examples of the divalent hydrocarbon group having from 2 to 8 carbon atoms, in General Formula (IIID), include alkylene groups, arylene groups, and alkenylene groups. Specific examples thereof include ethylene group, trimethylene group, tetramethylene group, 1,2-phenylene group, and vinylene group.

Accordingly, in General Formula (IIIC), examples of preferred combination of ($R^7$, $R^8$, $R^9$, $R^{10}$, s, t, u) include: (methyl group, phenyl group, methyl group, methyl group, 1, 1, 1), (methyl group, phenyl group, methyl group, ethyl group, 1, 1, 1), (phenyl group, -, methyl group, methyl group, 1,0,1), (phenyl group, -, methyl group, methyl group, 1, 0, 2), (phenyl group, vinyl group, ethyl group, 1, 1, 1), (vinyl group, -, ethyl group, methyl group, 1, 0, 1), (vinyl group, -, ethyl group, methyl group, 1, 0, 2), (vinyl group, -, methyl group, methyl group, 1, 0, 1), (vinyl group, -, methyl group, methyl group, 1, 0, 2), (hexyl group, -, ethyl group, methyl group, 1, 0, 1), (hexyl group, -, ethyl group, methyl group, 1, 0, 2), (phenyl group, -, ethyl group, methyl group, 1, 0, 1), (phenyl group, -, ethyl group, methyl group, 1, 0, 2), (3,3,3-trifluoropropyl group, -, methyl group, methyl group, 1, 0, 1), (3,3,3-trifluoropropyl group, -, methyl group, methyl group, 1, 0, 2), (1H,1H,2H,2H-tridecafluorooctyl group, -, ethyl group, methyl group, 1, 0, 1), (1H,1H,2H, 2H-tridecafluorooctyl group, -, ethyl group, methyl group, 1, 0, 2), (1H,1H,2H,2H-heptadecafluorodecyl group, -, ethyl group, methyl group, 1, 0, 1), (1H,1H,2H,2H-heptadecafluorodecyl group, -, ethyl group, methyl group, 1, 0, 2), (methyl group, -, ethyl group, trichloromethyl group, 2, 0, 1), and (-, -, ethyl group, trichloromethyl group, 0, 0, 1).

Further, in General Formula (IIID), examples of preferred combination of ($R^{11}$, $R^{12}$, $R^{13}$, $R^{14}$, $R^{15}$, v, w, x, y) include (methyl group, methyl group, methyl group, ethyl group, ethylene group, 1, 1, 1, 1), (methyl group, methyl group, methyl group, ethyl group, trimethylene group, 1, 1, 1, 1), (methyl group, methyl group, methyl group, methyl group, ethyl group, cyclohexane-1,2-diylgroup, 1, 1, 1, 1), (methyl group, methyl group, methyl group, methyl group, ethyl group, 1,2-phenylene group, 1, 1, 1, 1), (methyl group, methyl group, methyl group, ethyl group, and vinylene group, 1, 1, 1, 1).

The reaction step in the present invention is, in other words, a reaction step which involves a nucleophilic substitution reaction by a carboxylic anhydride on a starting alkoxysilane containing an alkoxy group.

Accordingly, in cases where an acyclic carboxylic anhydride represented by the above described General Formula (IIA) is used, the reaction in the present invention involves the elimination of a carboxylic acid ester. In the case of the reaction of a monoalkoxysilane, the reaction step thereof can be represented, for example, by the following reaction formula.

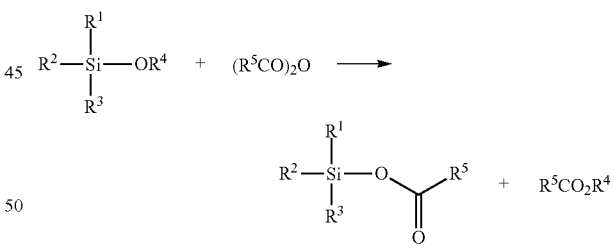

On the other hand, in the case of using a cyclic carboxylic anhydride represented by the above described General Formula (IIB), the reaction in the present invention does not involve the elimination of a carboxylic acid ester, differing from the case in which the acyclic carboxylic anhydride is used, and the reaction step thereof can be represented, for example, by the following reaction formula.

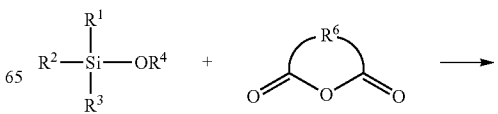

-continued

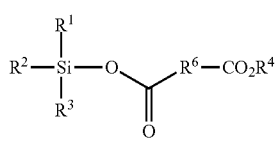

Specifically, in the case of using the cyclic carboxylic anhydride, an acyloxysilane is obtained having a structure in which the cyclic carboxylic anhydride is inserted into the silicon-oxygen bond of the starting alkoxysilane.

In each of these reactions, the starting alkoxysilane may be any of a monoalkoxysilane, a dialkoxysilane, a trialkoxysilane, and a tetraalkoxysilane.

Therefore, in the reaction in which the acyclic carboxylic anhydride is used, for example, it is possible to obtain acyloxysilanes represented by the following reaction formulae:

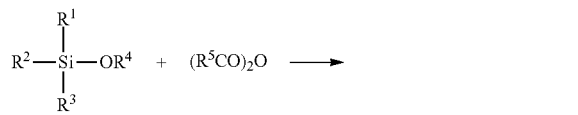

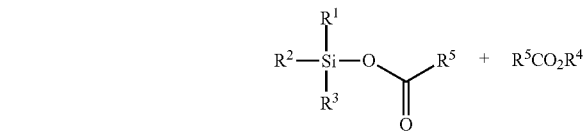

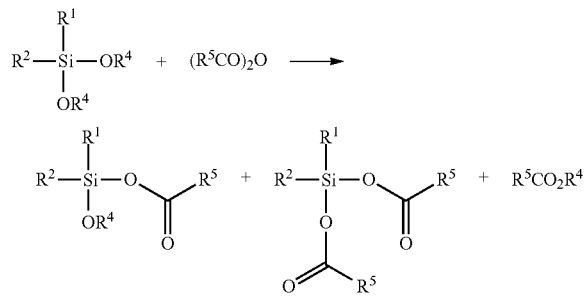

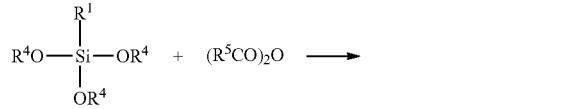

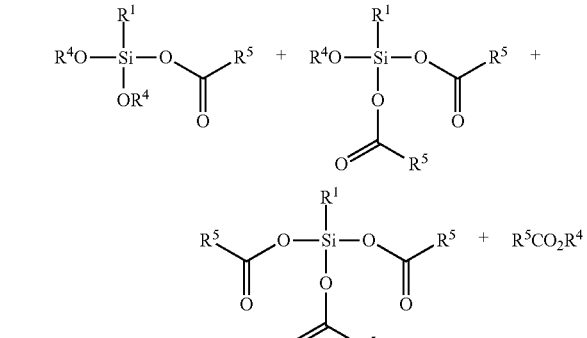

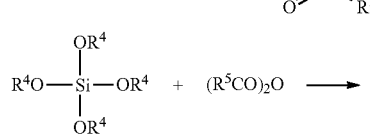

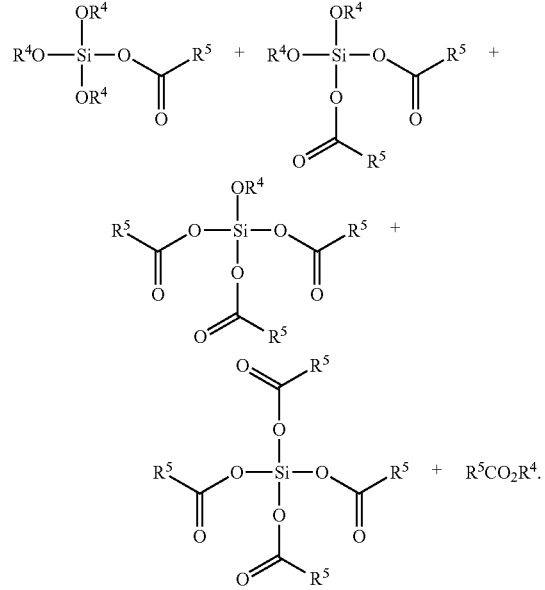

Specifically, this means as follows. In cases where a monoalkoxysilane is used as a raw material, namely, as a starting material, in the reaction step of the present invention, one type of acyloxysilane is obtained. However, in cases where a dialkoxysilane, a trialkoxysilane, or a tetraalkoxysilane is used as the starting material, the resulting acyloxysilane is not limited to one type. For example, in cases where a dialkoxysilane is used as the starting material, the resulting acyloxysilane may be an acyloxysilane in which one alkoxy group is substituted, an acyloxysilane in which two alkoxy groups are substituted, or a mixture thereof. Further, in cases where a trialkoxysilane is used as the starting material, the resulting acyloxysilane may be an acyloxysilane in which one alkoxy group is substituted, an acyloxysilane in which two alkoxy groups are substituted, an acyloxysilane in which three alkoxy groups are substituted, or a mixture thereof. In addition, in cases where a tetraalkoxysilane is used as the starting material, the resulting acyloxysilane may be an acyloxysilane in which one alkoxy group is substituted, an acyloxysilane in which two alkoxy groups are substituted, an acyloxysilane in which three alkoxy groups are substituted, an acyloxysilane in which four alkoxy groups are substituted, or a mixture thereof.

An acyloxysilane provided by the production method according to the present generally has a higher reactivity as compared to an alkoxysilane to be used as the starting material, due to containing an acyloxy group having a higher reactivity than an alkoxy group. Therefore, in cases where the thus obtained acyloxysilane is used as a synthetic intermediate, or as a surface treatment agent, a sol/gel material or the like, it is thought that the reaction thereof can be carried out more efficiently, under the conditions which are milder than those in the case of using an alkoxysilane to be used as the starting material. Therefore, an acyloxysilane provided by the present production method has a high utility value as a functional chemical.

In the reaction step of producing an acyloxysilane according to the present invention, it is possible to use any of various types of conventionally known acid catalysts, in order to accelerate the reaction.

The acid catalyst to be used may be a solid acid catalyst, whose separation, collection and the like can be carried out easily. Specific examples of the solid acid catalyst include solid inorganic substances such as metal salts and metal oxides. More specific examples thereof include: zeolites, mesoporous silicas, montmorillonites and the like containing protic hydrogen atoms or metal cations (of aluminum, titanium, gallium, iron, cerium, scandium or the like), as well as silica gel, heteropoly acids, and inorganic solid acids containing a carbon-based material as a carrier.

Among these, preferred in terms of catalytic activity and selectivity of products, for example, are zeolite-based, mesoporous silica-based and montmorillonite-based solid acids and the like, which are inorganic solid acids having a regular pore structure and/or a layered structure. More preferred are zeolite-based and montmorillonite-based solid acids. The type(s) of the regular pore structure and/or the layered structure of the inorganic solid acid is/are not particularly limited. However, the solid acid catalyst having a pore structure has a pore diameter within the range of from 0.2 to 20 nm, preferably from 0.3 to 15 nm, and more preferably from 0.3 to 10 nm, in terms of facilitating the diffusion of reacting molecules and generated molecules. Further, the solid acid catalyst having a layered structure has an interlayer distance within the range of from 0.2 to 20 nm, preferably from 0.3 to 15 nm, and more preferably from 0.3 to 10 nm.

In the case of using a zeolite as the inorganic solid acid catalyst having a regular pore structure, it is possible to use any of various types of zeolites having, for example, a Y-type, a beta-type, a ZSM-5-type, a mordenite-type, or a SAPO-type basic skeleton. In addition, a USY-type (Ultrastable Y) zeolite can also be preferably used, which is obtained by subjecting a Y-type zeolite (Na—Y) to a secondary treatment, and which is known, for example, as a SUSY-type (Super Ultrastable Y) zeolite, a VUSY-type (Very Ultrastable Y) zeolite, a SDUSY-type (Super dealuminated ultrastable Y) zeolite, or the like (regarding USY-type zeolites, see, for example, "Molecular Sieves" Advances in Chemistry, Volume 121, American Chemical Society, 1973, Chapter 19, and the like).

In terms of reaction rate, preferred among the above mentioned zeolites are a USY-type zeolite, a beta-type zeolite, a Y-type zeolite, a ZSM-5-type zeolite and a mordenite-type zeolite; more preferred are a USY-type zeolite, a beta-type zeolite and a Y-type zeolite; and still more preferred are a USY-type zeolite and a beta-type zeolite. Further, a USY-type zeolite and a beta-type zeolite are also preferred as a zeolite for selectively converting some or all of a plurality of alkoxy groups to an acyloxy group(s).

It is possible to use any of various types of the above mentioned zeolites, such as for example, a Bronsted acid type containing protic hydrogen atoms or a Lewis acid type containing metal cations. In particular, a protonated type thereof containing protic hydrogen atoms is referred to as, for example, an H-Y-type, H-SDUSY-type, H-SUSY-type, H-beta-type, H-mordenite-type or H-ZSM-5-type zeolite. Further, it is also possible to use a zeolite converted to a protonated type, by calcining an ammonium-type zeolite such as an $NH_4$-Y-type, $NH_4$-VUSY-type, $NH_4$-beta-type, $NH_4$-mordenite-type, or $NH_4$-ZSM-5-type zeolite.

Further, the silica/alumina ratio (amount of substance ratio) in the zeolite can be selected from various ratios, depending on the reaction conditions. However, the silica/alumina ratio is usually from 3 to 1,000, preferably from 3 to 800, more preferably from 5 to 600, and still more preferably from 5 to 400.

Various types of zeolites, including commercially available products, of the above described zeolites can be used. Specific examples of the commercially available products include the following. Examples of the USY-type zeolite include CBV 760, CBV 780, CBV 720, CBV 712, and CBV600, available from Zeolyst International. Examples of the Y-type zeolite include HSZ-360 HOA and HSZ-320 HOA, available from Tosoh Corporation. Examples of the beta-type zeolite include: CP811C, CP814N, CP7119, CP814E, CP7105, CP814CN, CP811TL, CP814T, CP814Q, CP811Q, CP811E-75, CP811E, and CP811C-300, available from Zeolyst International; HSZ-930HOA and HSZ-940HOA available from Tosoh Corporation; and UOP-Beta available from UOP Co. Examples of the mordenite-type zeolite include: CBV21A and CBV90A available from Zeolyst International; and HSZ-660HOA, HSZ-620HOA and HSZ-690HO available from Tosoh Corporation. Examples of the ZSM-5-type zeolite include CBV5524G, CBV8020 and CBV8014N available from Zeolyst International.

In addition to the above described inorganic solid acid, an organic solid acid containing an acid functional group can also be used effectively. The organic solid acid is, for example, a polymer containing an acid functional group. Examples of the acid functional group include sulfo group, carboxy group and phosphoryl group. Examples of the polymer include Teflon (registered trademark) skeleton polymers having perfluoro side chains, and styrene-divinylbenzene copolymers. Specific examples thereof include sulfo group-containing polymers such as Nafion (registered trademark, available from DuPont Company), Dowex (registered trademark, available from The Dow Chemical Company), Amberlite (registered trademark, available from Rohm and Haas Co.), and Amberlyst (registered trademark, available from The Dow Chemical Company). More specific examples thereof include Nafion NR50, Dowex 50WX2, Dowex 50WX4, Dowex 50WX8, Amberlite IR120, Amberlite IRP-64, Amberlyst 15, and Amberlyst 36. In addition, it is also possible to use a catalyst (such as Nafion SAC-13) in which an organic solid acid such as Nafion is supported on an inorganic substance such as silica. A plurality of inorganic solid acids and organic solid acids can also be used in combination.

Further, an inorganic or organic acid other than the solid acids, having Bronsted acidity or Lewis acidity, can also be used as the catalyst. Specific examples thereof include the following. Examples of the inorganic acid as described above include Bronsted-acidic compounds such as sulfuric acid, nitric acid, and hydrochloric acid; and Lewis-acidic compounds such as scandium (III) chloride, yttrium (III) chloride, titanium (III or IV) chloride, iron (III) chloride, iron (III) bromide, iron (III) perchlorate, ruthenium (III) chloride, zinc (II) chloride, boron (III) fluoride, boron (III) chloride, aluminum (III) chloride, aluminum (III) bromide, gallium (III) chloride, indium (III) chloride, tin (IV) chloride, and bismuth (III) chloride. These compounds may be used in the form of a hydrate. Examples of the organic acid as described above include Bronsted-acidic compounds such as trifluoromethanesulfonic acid, pentafluoroethanesulfonic acid, nonafluorobutanesulfonic acid, methanesulfonic acid, p-toluenesulfonic acid, bis(trifluoromethanesulfonyl)imide, and bis(nonafluorobutanesulfonyl)imide. In addition, metal salts of the above mentioned Bronsted-acidic compounds, tris(pentafluorophenyl)borane and the like, which are Lewis-acidic compounds, can also be used as the organic acid. Examples of metal cations in the Lewis-acidic metal salts include cations of metals such as scandium (III), yttrium (III), iron (III), cobalt (II), copper (II), silver (I), zinc (II), tin (II), bismuth (III) and the like; as well as lanthanoid elements such as lanthanum (III), praseodymium (III), samarium (III), neodymium (III), and ytterbium (III).

Among the above mentioned compounds, an inorganic acid which is preferred in terms of catalytic activity is a chloride, a bromide, a perchlorate or the like, containing an element selected from iron, ruthenium, aluminum, scandium, tin or indium. Specific examples thereof include iron (III) chloride, iron (III) bromide, iron (III) perchlorate, ruthenium (III) chloride, indium (III) chloride, and tin (IV) chloride. In addition, it is also a preferred method to add silver perchlorate or the like to a chloride or a bromide containing such an element, to convert the chloride or the bromide to a perchlorate, to be used as the catalyst.

Further, a preferred organic acid is a sulfonic acid, a sulfonylimide or the like, and also preferred is a salt formed from any of these acids, and an element selected from iron, ruthenium, aluminum, scandium, tin, indium or the like. Specific examples of the sulfonic acid and the sulfonylimide include trifluoromethanesulfonic acid, nonafluorobutanesulfonic acid, methanesulfonic acid, and bis(trifluoromethanesulfonyl)imide. Examples of cations of the element which forms a salt with any of these compounds include cations of scandium (III), iron (III), ruthenium (III), aluminum (III), gallium (III), indium (III), bismuth (III), and tin (IV). A plurality of the above mentioned inorganic acids and organic acids other than the solid acids can be used in combination. It is also possible to use any of the inorganic acids and organic acids in combination with any of the above mentioned solid acids.

The amount of catalyst with respect to the amount of raw materials, namely, starting materials to be reacted, can be selected arbitrarily. However, the amount of catalyst is usually from about 0.0001 to 10, preferably from about 0.001 to 8, and more preferably from about 0.001 to 6, in a weight ratio.

The reaction of the present invention can be carried out in a liquid phase state or gas phase state, depending on the reaction temperature and the reaction pressure. The reactor to be used for the reaction may be of any of various forms hitherto known, such as a batch type reactor, a flow type reactor or the like.

The reaction temperature is usually −20° C. or higher, preferably from −10 to 300° C., and more preferably from −10 to 200° C. In cases where the reaction is carried out at room temperature in order to control the reactivity of an alcohol, the room temperature is usually within the range of from 0 to 40° C., preferably from 5 to 40° C., and more preferably from 10 to 35° C.

The reaction pressure is usually from 0.1 to 100 atmospheres, preferably from 0.1 to 50 atmospheres, and more preferably from 0.1 to 10 atmospheres.

The reaction time depends on, for example, the amount of the starting materials and of the catalyst, the reaction temperature, the form of the reactor used, and the like. However, in view of productivity and efficiency, the reaction time is usually about from 0.1 to 1,200 minutes, preferably from 0.1 to 600 minutes, and more preferably from 0.1 to 300 minutes.

In cases where the reaction is carried out in a liquid phase system, the reaction can take place regardless of the presence or absence of a solvent. In the case of using a solvent, it is possible to use any of various types of solvents, excluding those which react with the starting materials. Examples of the solvents which can be used include hydrocarbons such as decalin (decahydronaphthalene) and decane; halogenated hydrocarbons such as chlorobenzene, 1,2- or 1,3-dichlorobenzene, and 1,2,3- or 1,2,4-trichlorobenzene; and ethers such as tert-butyl methyl ether and dibutyl ether. Two or more of the solvents may be used as a mixture. Further, in cases where the reaction is carried out in a gas phase system, an inert gas such as nitrogen or the like can be added to the gas phase, to carry out the reaction.

The reaction of the present invention can also be carried out under microwave irradiation. In the reaction system of the invention, the carboxylic anhydride used as a starting material, the acid catalyst and the like have a relatively high dielectric loss factor, and absorb microwaves efficiently. Therefore, the carboxylic anhydride, the catalyst and the like are activated under microwave irradiation, and thus the reaction can be carried out more efficiently.

In a reaction under microwave irradiation, it is possible to use any of various types of commercially available apparatuses equipped with a contact or non-contact temperature sensor, or the like. Further, the output of microwave irradiation, the type of cavity (multi mode, single mode), the form of irradiation (continuous, intermittent) and the like can be selected arbitrarily, depending on the scale, type and the like of the reaction. The frequency of the microwaves is usually within the range of from 0.3 to 30 GHz. Within the above range, preferred is the IMS frequency band which is assigned for use in the field of industry, science and medicine. More preferred within the IMS frequency band, in particular, is a 2.45 GHz band, a 5.8 GHz band, or the like.

Further, in the reaction under microwave irradiation, it is possible to add a heating material (susceptor), which absorbs microwaves and generates heat, to the reaction system, in order to more efficiently heat the reaction system. Any of various types of conventionally known heating materials can be used, such as for example, activated carbon, graphite, silicon carbide, titanium carbide, or the like. Further, it is also possible to use a molded catalyst, obtained by mixing powders of the above described catalyst and the heating material, adding thereto an adequate binder such as sepiolite, hormite or the like, and subjecting the resulting mixture to a calcination process.

Although the reaction step of the present invention proceeds in a closed-system reactor, it is also possible to allow the reaction to proceed more efficiently, by using an open-system reactor, and continuously removing the reaction product(s) out of the reaction system.

In cases where a solid acid catalyst is used in the production method according to the present invention, the separation and the collection of the catalyst after the completion of the reaction step can be carried out easily, by a method such as filtration, centrifugal separation, or the like.

Further, the purification of the resulting acyloxysilane can also be achieved by means of distillation, recrystallization, column chromatography, and the like, which are commonly used in organic chemistry.

Since an acyloxysilane provided by the production method according to the present invention contains an acyloxy group having a higher reactivity than an alkoxy group, the resulting acyloxysilane has a higher reactivity as compared to the starting alkoxysilane, and thus has a high utility value as a functional chemical, such as a synthetic intermediate or a surface treatment agent.

For example, in cases where the thus obtained acyloxysilane is used as a surface treatment agent, the surface treatment of a solid material such as glass can be quickly carried out, within a period of time of several minutes, at room temperature under mild conditions. At this time, the hydrophilicity/hydrophobicity of the surface of the solid material can be easily controlled, by properly selecting the type of the acyloxysilane to be used.

The surface treatment agent according to the present invention contains an acyloxysilane produced by the above described reaction step, and it is possible to use, not only the resulting acyloxysilane which has then been isolated and purified, but also a mixed solution containing a plurality of acyloxysilanes.

Further, since, in the production method according to the present invention, it is possible to easily produce an acyloxysilane of a variety of types under mild conditions, using an easily available alkoxysilane as a starting material, a reaction liquid containing the resulting acyloxysilane can be used as it is for carrying out a surface treatment, and this surface treatment method is also characteristic to the present invention.

In cases where the acyloxysilane is used as the surface treatment agent, an organic solvent which does not react with the acyloxysilane, such as toluene or hexane, may be used to dilute the acyloxysilane, as necessary.

The surface treatment of a solid material can be carried out using any of various types of conventionally known methods, such as for example, a dip method (immersion method), a cast method, a spin coating method, or a spray coating method.

EXAMPLES

The present invention will now be described with reference to Examples and Comparative Examples. However, the present invention is in no way limited to these Examples.

Example 1

A mixture of 3.2 mmol of (ethoxy)trimethylsilane (Ia), 6.4 mmol of acetic anhydride (IIAa) and 5 mg of zeolite: CBV780 (manufactured by Zeolyst International) was introduced into a reaction tube, and the mixture was stirred at 110° C. for five minutes, using a microwave irradiation apparatus (Initiator; manufactured by Biotage AB). The resulting product was analyzed by a gas chromatograph and a gas chromatograph mass spectrometer, and the yield of the product was measured by a gas chromatograph. As a result, it was confirmed that (acetoxy)trimethylsilane (IIIAa) had been formed with a yield of 89% (see Table 1-1).

Examples 2 to 85 and Comparative Examples 1 and 2

The same procedure as in Example 1 was repeated with varying reaction conditions (such as catalysts, starting materials, reaction temperature, reaction time and the like), to carry out reactions, and the analyses of the resulting products. The results of the yields of the respective products as measured by gas chromatography or nuclear magnetic resonance spectroscopy are shown in Table 1-1 to Table 1-7.

TABLE 1-1

| Example | I[1] (mmol) | II[2] (mmol) | Catalyst[3] (mg) | $SiO_2/Al_2O_3$ | Heating method[4] | Temp. (° C.) | Time (min) | III[5] | Yield[6] |
|---|---|---|---|---|---|---|---|---|---|
| Example 1 | Ia (3.2) | IIAa (6.4) | CBV780 (5) | 80.9 | MW | 110 | 5 | IIIAa | 89 |
| Example 2 | Ia (3.2) | IIAa (6.4) | CBV600 (5) | 5.5 | MW | 110 | 5 | IIIAa | 69 |
| Example 3 | Ia (3.2) | IIAa (6.4) | CP811E-75 (5) | 75 | MW | 110 | 5 | IIIAa | 78 |
| Example 4 | Ia (3.2) | IIAa (6.4) | HSZ-320HOA (5) | 5.4 | MW | 110 | 5 | IIIAa | 9 |
| Example 5 | Ia (3.2) | IIAa (6.4) | HSZ-830HOA (5) | 29 | MW | 110 | 5 | IIIAa | 8 |
| Example 6 | Ia (3.2) | IIAa (6.4) | NR50 (5) | — | MW | 110 | 5 | IIIAa | 35 |
| Example 7 | Ia (3.2) | IIAa (6.4) | Amberlyst15 (5) | — | MW | 110 | 5 | IIIAa | 23 |
| Example 8 | Ia (3.2) | IIAa (6.4) | Mont-Al$^{3+}$ (5) | — | MW | 110 | 5 | IIIAa | 75 |
| Example 9 | Ia (2.0) | IIAa (2.2) | CBV780 (5) | 80.9 | — | 25 | 60 | IIIAa | 95 |
| Example 10 | Ia (2.0) | IIAa (2.2) | CBV780 (5) | 80.9 | MW | 60 | 5 | IIIAa | ≥99 |
| Example 11 | Ia (2.0) | IIAb (2.2) | CBV780 (5) | 80.9 | MW | 60 | 5 | IIIAb | ≥99 |
| Example 12 | Ia (2.0) | IIAc (2.2) | CBV780 (5) | 80.9 | MW | 100 | 5 | IIIAc | 96 |
| Example 13 | Ia (2.0) | IIAd (2.2) | CBV780 (5) | 80.9 | — | 25 | 60 | IIIAd | 81 |
| Example 14 | Ia (2.0) | IIAd (2.2) | CBV780 (5) | 80.9 | MW | 60 | 5 | IIIAd | 94 |
| Example 15 | Ia (2.0) | IIAe (2.2) | CBV780 (5) | 80.9 | MW | 80 | 5 | IIIAe | 57 |
| Example 16 | Ia (2.0) | IIAf (2.2) | CBV780 (5) | 80.9 | MW | 100 | 5 | IIIAf | 84 |
| Example 17 | Ia (2.0) | IIAf (2.2) | CBV780 (5) | 80.9 | MW | 120 | 5 | IIIAf | ≥99 |
| Example 18 | Ib (1.6) | IIAa (6.4) | CBV780 (5) | 80.9 | MW | 110 | 5 | IIIAg | ≥99 |
| Example 19 | Ic (1.6) | IIAa (6.4) | CBV780 (20) | 80.9 | MW | 110 | 20 | IIIAh | 97 |
| Example 20 | Id (1.7) | IIAa (6.6) | CBV780 (5) | 80.9 | MW | 25 | 2 | IIIAi (≥99:1) | 69 |
| Example 21 | Id (1.7) | IIAa (6.6) | CBV780 (5) | 80.9 | MW | 110 | 5 | IIIAi (≤1:99) | 89 |
| Example 22 | Id (1.7) | IIAa (6.5) | CBV600 (5) | 5.5 | MW | 110 | 5 | IIIAi (≥99:1) | 66 |
| Example 23 | Id (1.7) | IIAa (6.6) | Amberlyst15 (5) | — | MW | 110 | 5 | IIIAi (92:8) | 34 |
| Example 24 | Id (5.0) | IIAb (7.4) | CBV780 (15) | 80.9 | — | 25 | 20 | IIIAj (93:7) | 89 |
| Example 25 | Id (5.0) | IIAb (14.9) | CBV780 (30) | 80.9 | MW | 110 | 30 | IIIAj (≤1:99) | ≥99 |

TABLE 1-2

| Example | I[1] (mmol) | II[2] (mmol) | Catalyst[3] (mg) | $SiO_2/Al_2O_3$ | Heating method[4] | Temp. (° C.) | Time (min) | III[5] | Yield[6] |
|---|---|---|---|---|---|---|---|---|---|
| Example 26 | Ie (1.0) | IIAb (4.0) | CBV780 (5) | 80.9 | MW | 60 | 5 | IIIAk (96:4) | 96 |
| Example 27 | If (1.6) | IIAa (2.4) | CBV780 (5) | 80.9 | — | 25 | 30 | IIIAl (≥99:1:0) | 90 |
| Example 28 | If (1.6) | IIAa (6.4) | CBV780 (20) | 80.9 | MW | 50 | 20 | IIIAl (15:68:17) | ≥99 |
| Example 29 | Ig (2.0) | IIAa (2.2) | CBV780 (5) | 80.9 | MW | 60 | 5 | IIIAm (98:2:0) | 62 |
| Example 30 | Ih (2.0) | IIAa (2.2) | CBV780 (5) | 80.9 | — | 25 | 20 | IIIAn (98:2:0) | 86 |
| Example 31 | Ii (2.0) | IIAa (2.2) | CBV780 (20) | 80.9 | — | 25 | 20 | IIIAo (≥99:1:0:0) | 81 |
| Example 32 | Ii (1.6) | IIAb (2.4) | CBV780 (30) | 80.9 | — | 25 | 30 | IIIAp (97:3:0:0) | 92 |
| Example 33 | Ij (2.0) | IIAa (2.2) | CBV780 (20) | 80.9 | — | 25 | 20 | IIIAq (≥99:1:0:0) | 81 |
| Example 34[7] | Ia (1.6) | IIBa (1.3) | CBV780 (10) | 80.9 | MW | 120 | 30 | IIIBa | 82 |
| Example 35[7] | Ia (1.6) | IIBa (1.3) | CBV600 (10) | 5.5 | MW | 120 | 30 | IIIBa | 58 |
| Example 36[7] | Ia (1.6) | IIBa (1.3) | CP811E-75 (10) | 75 | MW | 120 | 30 | IIIBa | 81 |
| Example 37[7] | Ia (1.6) | IIBa (1.3) | CP811C-300 (10) | 243 | MW | 120 | 30 | IIIBa | 73 |
| Example 38[7] | Ia (1.6) | IIBa (1.3) | HSZ-320HOA (10) | 5.4 | MW | 120 | 30 | IIIBa | 29 |
| Example 39[7] | Ia (1.6) | IIBa (1.3) | HSZ-830HOA (10) | 29 | MW | 120 | 30 | IIIBa | 5 |
| Example 40[7] | Ia (1.6) | IIBa (1.3) | NR50 (10) | — | MW | 120 | 30 | IIIBa | 26 |
| Example 41[7] | Ia (1.6) | IIBa (1.3) | Amberlyst15 (10) | — | MW | 120 | 30 | IIIBa | 7 |
| Example 42[7] | Ia (1.6) | IIBa (1.3) | Mont-Al$^{3+}$ (10) | — | MW | 120 | 30 | IIIBa | 64 |
| Example 43[7] | Ia (1.6) | IIBb (1.3) | CBV780 (10) | 80.9 | MW | 120 | 30 | IIIBb | 70 |
| Example 44[7] | Ia (1.6) | IIBc (1.3) | CBV780 (10) | 80.9 | MW | 120 | 30 | IIIBc | 65 |
| Example 45[7] | Ia (1.6) | IIBd (1.3) | CBV780 (10) | 80.9 | MW | 150 | 30 | IIIBd | 25 |
| Example 46[7] | Ia (1.6) | IIBe (1.3) | CBV780 (10) | 80.9 | MW | 150 | 30 | IIIBe | 30 |
| Example 47[8] | Id (2.0) | IIBa (1.3) | CBV780 (15) | 80.9 | MW | 140 | 30 | IIIBf (96:4) | 50 |
| Example 48 | Ia (2.0) | IIAc (2.2) | CBV780 (5) | 80.9 | MW | 60 | 5 | IIIAc | 41 |
| Example 49 | Ia (2.0) | IIAc (2.2) | CBV780 (5) | 80.9 | OB | 60 | 5 | IIIAc | 36 |
| Example 50 | Ia (2.0) | IIAc (2.2) | CBV780 (5) | 80.9 | MW | 80 | 5 | IIIAc | 81 |

TABLE 1-3

| Example | I[1] (mmol) | II[2] (mmol) | Catalyst[3] (mg) | $SiO_2/Al_2O_3$ | Heating method[4] | Temp. (° C.) | Time (min) | III[5] | Yield[6] (%) |
|---|---|---|---|---|---|---|---|---|---|
| Example 51 | Ia (2.0) | IIAc (2.2) | CBV780 (5) | 80.9 | OB | 80 | 5 | IIIAc | 73 |
| Example 52[7] | Ia (1.6) | IIBa (1.3) | CBV780 (5) | 80.9 | MW | 120 | 5 | IIIBa | 42 |
| Example 53[7] | Ia (1.6) | IIBa (1.3) | CBV780 (5) | 80.9 | OB | 120 | 5 | IIIBa | 32 |
| Example 54[7] | Ia (1.6) | IIBa (1.3) | CBV780 (5) | 80.9 | MW | 120 | 15 | IIIBa | 70 |
| Example 55[7] | Ia (1.6) | IIBa (1.3) | CBV780 (5) | 80.9 | OB | 120 | 15 | IIIBa | 65 |
| Comparative Example 1 | Ii (2.0) | IIAa (2.2) | — | — | — | 25 | 20 | IIIAo | 0 |
| Comparative Example 2 | Ii (2.0) | IIAa (2.2) | — | — | OB | 100 | 20 | IIIAo | 0 |
| Example 56 | Ia (3.2) | IIAa (6.4) | $FeCl_3$ (2.6)[9] | — | — | 25 | 5 | IIIAa | 98 |
| Example 57 | Ia (3.2) | IIAa (6.4) | $FeBr_3$ (4.7)[9] | — | — | 25 | 5 | IIIAa | ≥99 |
| Example 58 | Ia (3.2) | IIAa (6.4) | $Fe(ClO_4)_3 \cdot 6H_2O$ (7.4)[9] | — | — | 25 | 5 | IIIAa | ≥99 |
| Example 59 | Ia (3.2) | IIAa (6.4) | $RuCl_3 \cdot H_2O$ (3.6)[9] | — | — | 25 | 5 | IIIAa | ≥99 |
| Example 60 | Ia (3.2) | IIAa (6.4) | $SnCl_4 \cdot 5H_2O$ (5.6)[9] | — | — | 25 | 5 | IIIAa | 91 |
| Example 61 | Ia (3.2) | IIAa (6.4) | $InCl_3$ (3.5)[9] | — | — | 25 | 30 | IIIAa | 93 |
| Example 62 | Ia (3.2) | IIAa (6.4) | $CF_3SO_3H$ (2.4)[9] | — | — | 25 | 5 | IIIAa | 95 |
| Example 63 | Ia (3.2) | IIAa (6.4) | $Fe(OSO_2CF_3)_3$ (8.1)[9] | — | — | 25 | 5 | IIIAa | 98 |
| Example 64 | Ia (3.2) | IIAa (6.4) | $Al(OSO_2CF_3)_3$ (7.6)[9] | — | — | 25 | 5 | IIIAa | 97 |
| Example 65 | Ii (2.0) | IIAa (12) | $FeCl_3$ (1.6)[9] | — | — | 25 | 30 | IIIAo (66:39:5:0) | ≥99 |
| Example 66 | Ii (2.0) | IIAa (12) | $RuCl_3 \cdot H_2O$ (2.3)[9] | — | — | 25 | 5 | IIIAo (50:45:5:0) | ≥99 |
| Example 67 | Ii (2.0) | IIAa (12) | $RuCl_3 \cdot H_2O$ (2.3)[9] + $AgClO_4$ (6.2) | — | — | 25 | 30 | IIIAo (10:69:21:0) | ≥99 |
| Example 68 | Ii (2.0) | IIAa (12) | $Al(OSO_2CF_3)_3$ (4.7)[9] | — | — | 25 | 30 | IIIAo (0:15:65:20) | ≥99 |
| Example 69 | Ii (2.0) | IIAa (12) | $Fe(ClO_4)_3 \cdot 6H_2O$ (4.6)[9] | — | — | 25 | 30 | IIIAa (0:0:23:77) | 84 |

TABLE 1-4

| Example | I[1] (mmol) | II[2] (mmol) | Catalyst[3] (mg) | $SiO_2/Al_2O_3$ | Heating method[4] | Temp. (° C.) | Time (min) | III[5] | Yield[6] (%) |
|---|---|---|---|---|---|---|---|---|---|
| Example 70 | Ii (2.0) | IIAa (12) | $Sc[N(OSO_2CF_3)_2]_3$ (8.9)[9] | — | — | 25 | 30 | IIIAo (0:0:25:75) | 93 |
| Example 71 | Ii (2.0) | IIAa (12) | $In[N(OSO_2CF_3)_2]_3$ (9.6)[9] | — | — | 25 | 30 | IIIAo (0:1:30:69) | 91 |
| Example 72 | Ii (2.0) | IIAa (12) | $CF_3SO_3H$ (1.5)[9] | — | — | 25 | 30 | IIIAo (0:29:62:9) | ≥99 |
| Example 73[10] | Ii (2.0) | IIAa (12) | $Fe(ClO_4)_3 \cdot 6H_2O$ (4.6)[9] | — | — | 25 | 30 | IIIAo (4:91:5:0) | ≥99 |
| Example 74 | Ik (2.0) | IIAa (2.2) | CBV780 (10) | 80.9 | — | 25 | 20 | IIIAr (94:6:0) | 88 |
| Example 75 | Il (2.0) | IIAa (2.2) | CBV780 (10) | 80.9 | — | 25 | 20 | IIIAs (83:17:0) | 84 |
| Example 76 | Im (1.0) | IIAa (1.2) | CBV780 (7) | 80.9 | — | 25 | 20 | IIIAt (76:24:0) | 87 |
| Example 77 | In (1.0) | IIAa (1.2) | CBV780 (10) | 80.9 | OB | 90 | 15 | IIIAu (72:28:0) | 89 |
| Example 78 | Io (1.0) | IIAa (1.2) | CBV780 (10) | 80.9 | OB | 90 | 15 | IIIAv (72:28:0) | 88 |
| Example 79 | Ia (1.5) | IIAg (1.5) | $Fe(ClO_4)_3 \cdot 6H_2O$ (3.5)[9] | — | OB | 90 | 30 | IIIAw | 69 |
| Example 80 | Ia (0.7) | IIAh (0.7) | $Fe(ClO_4)_3 \cdot 6H_2O$ (1.6)[9] | — | OB | 120 | 30 | IIIAx | 85 |
| Example 81 | Ia (1.5) | IIAl (1.5) | $Fe(ClO_4)_3 \cdot 6H_2O$ (0.7)[11] | — | — | 25 | 30 | IIIAy | 96 |
| Example 82 | Ia (0.7) | IIAj (0.7) | $Fe(ClO_4)_3 \cdot 6H_2O$ (1.6)[9] | — | OB | 120 | 30 | IIIAz | 93 |
| Example 83 | Ia (0.5) | IIAk (0.5) | $Fe(ClO_4)_3 \cdot 6H_2O$ (2.3)[12] | — | OB | 180 | 20 | IIIAaa | 86 |
| Example 84 | Ip (4.5) | IIAi (4.5) | $Fe(ClO_4)_3 \cdot 6H_2O$ (2.1)[11] | — | OB | 80 | 20 | IIIAab (100:0) | 95 |
| Example 85 | Il (1.5) | IIAi (1.5) | $Fe(ClO_4)_3 \cdot 6H_2O$ (3.5)[9] | — | OB | 90 | 20 | IIIAac (100:0:0:0) | 83 |

1) Ia: (ethoxy)trimethylsilane, Ib: (ethoxy)dimethyl(phenyl)silane, Ic: (ethoxy)methyldi(phenyl)silane, Id: methyldi(methoxy)(phenyl)silane, Ie: di(ethoxy)(phenyl)silane, If: tri(methoxy)(phenyl)silane, Ig: tri(ethoxy)vinylsilane, Ih: tri(methoxy)vinylsilane, Ii: tetra(ethoxy)silane, Ij: tetra(methoxy)silane, Ik: tri(ethoxy)(hexyl)silane, Il: tri(ethoxy)(phenyl)silane, Im: (3,3,3-trifluoropropyl)tri(methoxy)silane, In: tri(ethoxy)(1H,1H,2H,2H-tridecafluorooctyl)silane, Io: tri(ethoxy)(1H,1H,2H,2H-heptadecafluorodecyl)silane, Ip: di(ethoxy)di(methyl)silane.

IIIAa: (acetoxy)trimethylsilane,
IIIAb: (propanoyloxy)trimethylsilane,
IIIAc: (hexanoyloxy)trimethylsilane,
IIIAd: (trifluoroacetoxy)trimethylsilane,
IIIAe: (crotonoyloxy)trimethylsilane,
IIIAf: (benzoyloxy)trimethylsilane,
IIIAg: (acetoxy)dimethyl(phenyl)silane,
IIIAh: (acetoxy)methyldi(phenyl)silane, 2) IIAa: acetic anhydride, IIAb: propionic anhydride, IIAc: hexanoic anhydride, IIAd: trifluoroacetic anhydride, IIAe: crotonic anhydride, IIAf: benzoic anhydride, IIAg: chloroacetic anhydride, IIAh: dichloroacetic anhydride, IIAi: trichloroacetic anhydride, IIAj: chlorodifluoroacetic anhydride, IIAk: pentafluorobenzoic anhydride, IIBa: succinic anhydride, IIBb: glutaric anhydride, IIBc: cyclohexane-1,2-dicarboxylic anhydride, IIBd: phthalic anhydride, IIBe: maleic anhydride.

3) All the zeolites have been calcined at 500° C., before being used.
CBV780: H-SDUSY-type zeolite, CBV780 (manufactured by Zeolyst International), CBV600: H-SUSY-type zeolite, CBV600 (manufactured by Zeolyst International), CP811E-75: H-beta-type zeolite, CP811E-75 (manufactured by Zeolyst International), CP811C-300: H-beta-type zeolite, CP811C-300 (manufactured by Zeolyst International),
CBV780: H-SDUSY-type zeolite, CBV780 (manufactured by Zeolyst International), HSZ-320HOA: H-Y-type zeolite, HSZ-320HOA (manufactured by Tosoh Corporation),
HSZ-830HOA: H-ZSM-5-type zeolite, HSZ-830HOA (manufactured by Tosoh Corporation),
NR50: Sulfo group-containing polymer, Nafion NR50 (manufactured by DuPont Company),
Amberlyst 15: Sulfo group-containing polymer, Amberlyst 15 (manufactured by The Dow Chemical Company),
$Al^{3+}$-Mont: $Al^{3+}$-containing montmorillonite (prepared by treating a $Na^+$-type montmorillonite with an $Al^{3+}$ solution).

4) MW: A microwave reaction apparatus, Initiator (manufactured by Biotage AB) was used; OB: an oil bath heating device, MH-5D (manufactured by RIKOH KAGAKU co., ltd.) was used.

5) In cases where an acyloxy product(s) including two or more acyloxy groups, namely a diacyloxy product, a triacyloxy product etc., coexist(s) with a monoacyloxy product, in each of the compounds III, the yield of the compound III represents the total yield of the monoacyloxy product (III-1), diacyloxy product (III-2), triacyloxy product (III-3), and/or tetraacyloxy product (III-4). The numbers shown in parentheses indicate the ratios of the respective products.

The respective products (IIIAa) to (IIIAq) and (IIIBa) to (IIIBe) are as follows:

TABLE 1-6

IIIAi-1: (acetoxy)methyl(methoxy)(phenyl)silane,
IIIAi-2: di(acetoxy)methyl(phenyl)silane,
IIIAj-1: methyl(methoxy)(phenyl)(propanoyloxy)silane,
IIIAj-2: methyl(phenyl)di(propanoyloxy)silane,
IIIAk-1: (acetoxy)(ethoxy)(phenyl)vinylsilane,
IIIAk-2: di(acetoxy)(phenyl)vinylsilane,
IIIAl-1: (acetoxy)di(methoxy)(phenyl)silane,
IIIAl-2: di(acetoxy)(methoxy)(phenyl)silane,
IIIAl-3: tri(acetoxy)(phenyl)silane,
IIIAm-1: (acetoxy)di(ethoxy)vinylsilane,
IIIAm-2: di(acetoxy)(ethoxy)vinylsilane,
IIIAm-3: tri(acetoxy)vinylsilane,
IIIAn-1: (acetoxy)di(methoxy)vinylsilane,
IIIAn-2: di(acetoxy)(methoxy)vinylsilane, TABLE 1-6-continued IIIAn-3: (IIIAm-3): tri(acetoxy)vinylsilane,
IIIAo-1: (acetoxy)tri(ethoxy)silane,
IIIAo-2: di(acetoxy)di(ethoxy)silane,
IIIAo-3: tri(acetoxy)(ethoxy)silane,
IIIAo-4: tetra(acetoxy)silane,
IIIAp-1: tri(ethoxy)(propanoyloxy)silane,
IIIAp-2: di(ethoxy)di(propanoyloxy)silane,
IIIAp-3: (ethoxy)tri(propanoyloxy)silane,
IIIAp-4: tetra(propanoyloxy)silane,
IIIAq-1: (acetoxy)tri(methoxy)silane,
IIIAq-2: di(acetoxy)di(methoxy)silane,
IIIAq-3: tri(acetoxy)methoxy)silane,
IIIAq-4 (IIIAo-4): tetra(acetoxy)silane,
IIIBa: [(3-ethoxycarbonyl)propanoyloxy]trimethylsilane,
IIIBb: [(4-ethoxycarbonyl)butanoyloxy]trimethylsilane,
IIIBc: [(2-ethoxycarbonyl)cyclohexanylcarbonyloxy]trimethylsilane,
IIIBd: [(2-ethoxycarbonyl)benzoyloxy]trimethylsilane,
IIIBe: [(3-ethoxycarbonyl)propenoyloxy]trimethylsilane,
IIIBf-1: [3-methoxycarbonyl)propanoyloxy]methyl(methoxy)(phenyl)silane,
IIIBf-2: di[(3-methoxycarbonyl)propanoyloxy]methyl(phenyl)silane,
IIIAr-1: (acetoxy)di(ethoxy)(hexyl)silane,
IIIAr-2: di(acetoxy)(ethoxy)(hexyl)silane,
IIIAr-3: tri(acetoxy)(hexyl)silane,
IIIAs-1: (acetoxy)di(ethoxy)(phenyl)silane,
IIIAs-2: di(acetoxy)(ethoxy)(phenyl)silane,
IIIAs-3 (IIIAl-3): tri(acetoxy)(phenyl)silane,
IIIAt-1: (acetoxy)(3,3,3-trifrluoropropyl)di(methoxy)silane,
IIIAt-2: di(acetoxy)(3,3,3-trifluoropropyl)(methoxy)silane,
IIIAt-3: tri(acetoxy)(3,3,3-trifrluoropropyl)silane,

TABLE 1-7

IIIAu-1: (acetoxy)di(ethoxy)(1H,1H,2H,2H-tridecafluorooctyl)silane,
IIIAu-2: di(acetoxy)(ethoxy)(1H,1H,2H,2H-tridecafluorooctyl)silane,
IIIAu-3: tri(acetoxy)(1H,1H,2H,2H-tridecafluorooctyl)silane,
IIIAv-1 : (acetoxy)di(ethoxy)(1H,1H,2H,2H-heptadecafluorodecyl)silane,
IIIAv-2: di(acetoxy)(ethoxy)(1H,1H,2H,2H-heptadecafluorodecyl)silane,
IIIAv-3: tri(acetoxy)(1H,1H,2H,2H-heptadecafluorodecyl)silane, TABLE 1-7-continued IIIAw: (chloroacetoxy)trimethylsilane,
IIIAx: (dichloroacetoxy)trimethylsilane,
IIIAy: (trichloroacetoxy)trimethylsilane,
IIIAz: (chlorodifluoroacetoxy)trimethylsilane,
IIIAaa: (pentafluorobenzoyl)trimethylsilane,
IIIAab-1: (trichloroacetoxy)(ethoxy)dimethylsilane,
IIIAab-2: bis(trichloroacetoxy)dimethylsilane,
IIIAac-1: (trichloroacetoxy)tri(ethoxy)silane,
IIIAac-2: bis(trichloroacetoxy)di(ethoxy)silane,
IIIAac-3: tris(trichloroacetoxy)(ethoxy)silane,
IIIAac-2: tetrakis(trichloroacetoxy)silane.

6) The respective yields were calculated by gas chromatography or nuclear magnetic resonance spectroscopy. In each of the reactions of IIAs, the yield with respect to I is shown, and in each of the reactions of IIBs, the yield with respect to IIB is shown.

7) 1,2-dichlorobenzene (2 ml) was used as a solvent.

8) 1,2-dichlorobenzene (1 mL) was used as a solvent.

9) The amount of catalyst was 0.5 mol % with respect to the amount of I.

10) Acetonitrile (1 mL) was used as a solvent.

11) The amount of catalyst was 0.1 mol % with respect to the amount of I.

12) The amount of catalyst was 1 mol % with respect to the amount of I.

The acyloxysilanes represented by General Formula (IIIA) or (IIIB) obtained in the above described Examples were analyzed, and the data of mass spectra and $^{29}$Si nuclear magnetic resonance spectra ($^{29}$Si-NMR) thereof are shown in Table 2-1 to Table 2-3. Further, in Table 2-1 to Table 2-3, in cases where the resulting acyloxysilanes correspond to the acyloxysilanes represented by the above described General Formula (IIIC) or (IIID), the compound numbers: (IIICs) or (IIIDs) are indicated in parentheses, after the compound numbers: (IIIAs) or (IIIBs).

TABLE 2-1

| Compound [1] | Fragment peak values of mass spectra, m/z (relative intensity) [2] | $^{29}$Si -NMR (δ, ppm) [3] |
|---|---|---|
| IIIAa | 117 (M$^+$—CH$_3$, 55), 75 (100), 73 (12), 45 (15), 43 (11) | 23.2 |
| IIIAb | 131 (M$^+$—CH$_3$, 56), 75 (100), 73 (45), 45 (17), 43 (11) | 23.0 |
| IIIAc | 173 (M$^+$—CH$_3$, 50), 132 (11), 131 (18), 117 (38), 75 (100), 73 (88), 45 (15), 43 (11) | 33.5 |
| IIIAd | 171 (M$^+$—CH$_3$, 2.9), 121 (29), 77 (100), 73 (42), 45 (13) | 23.0 |
| IIIAe | 158 (M$^+$, 0.3), 143 (100), 99 (47), 75 (87), 73 (20), 69 (20), 45 (15), 41 (14) | — |
| IIIAf | 194 (M$^+$, 7.0), 179 (100), 135 (88), 105 (94), 77 (62), 51 (16) | — |
| IIIAg | 179 (M$^+$—CH$_3$, 53), 137 (100), 117 (22), 75 (16), 45 (15) | 11.7 |
| IIIAh | 256 (M$^+$, 0.3), 241 (100), 199 (71), 178 (59), 137 (81), 77 (20), 45 (22) | 0.3 |
| IIIAi-1 (IIICi-1) | 195 (M$^+$—CH$_3$, 77), 153 (100), 133 (69), 123 (29), 91 (68), 61 (11), 45 (17) | −14.0 |
| IIIAi-2 | 223 (M$^+$—CH$_3$, 64), 181 (67), 161 (31), 139 (100), 137 (31), 119 (94), 91 (12), 77 (39), 45 (21), 43 (17) | −11.7 |
| IIIAj-1 (IIICj-1) | 209 (M$^+$—CH$_3$, 76), 153 (100), 151 (27), 147 (88), 123 (23), 121 (22), 91 (72), 45 (12) | −14.0 |
| IIIAj-2 | 251 (M$^+$—CH$_3$, 53), 195 (69), 193 (20), 189 (25), 139 (60), 137 (72), 133 (100), 91 (11), 77 (33), 45 (17) | −12.0 |
| IIIAk-1 (IIICk-1) | 236 (M$^+$, 2.3), 209 (100), 191 (13), 190 (19), 167 (49), 159 (47), 149 (25), 139 (56), 123 (34), 117 (41), 105 (14), 78 (12), 77 (17), 63 (18), 45 (29), 43 (13) | −32.2 |
| IIIAk-2 | 223 (M$^+$—CH=CH$_2$, 40), 190 (33), 181 (61), 173 (18), 149 (17), 148 (13), 139 (100), 131 (56), 123 (16), 121 (14), 89 (24), 77 (14), 45 (22), 43 (23) | −30.1 |

TABLE 2-1-continued

| Compound [1] | Fragment peak values of mass spectra, m/z (relative intensity) [2] | $^{29}$Si-NMR (δ, ppm) [3] |
|---|---|---|
| IIIA1-1 (IIIC1-1) | 226 (M$^+$, 4.8), 149 (100), 107 (52), 77 (12) | −57.4 |
| IIIA1-2 (IIIC1-2) | 223 (M$^+$—OCH$_3$, 0.4), 177 (58), 153 (24), 139 (13), 135 (100), 123 (14), 93 (26), 45 (12), 43 (13) | −60.3 |

TABLE 2-2

| Compound [1] | Fragment peak values of mass spectra, m/z (relative intensity) [2] | $^{29}$Si-NMR (δ, ppm) [3] |
|---|---|---|
| IIIAm-1 (IIICm-1) | 189 (M$^+$—CH$_3$, 0.7), 177 (100), 159 (59), 149 (16), 135 (61), 117 (53), 107 (24), 89 (29), 79 (27), 63 (31), 45 (17), 43 (16) | −60.8 |
| IIIAm-2 (IIICm-2) | 203 (M$^+$—CH$_3$, 0.5), 191 (41), 149 (100), 131 (63), 121 (18), 117 (25), 107 (32), 89 (37), 79 (26), 63 (22), 45 (12), 43 (25) | −62.3 |
| IIIAn-1 (IIICn-1) | 161 (M$^+$—CH$_3$, 0.3), 149 (100), 117 (15), 107 (76), 103 (19), 87 (11), 77 (29) | −58.3 |
| IIIAn-2 (IIICn-2) | 189 (M$^+$—CH$_3$, 0.8), 177 (32), 145 (11), 135 (100), 131 (11), 103 (34), 93 (45), 63 (16), 43 (20) | −60.7 |
| IIIAo-1 | 222 (M$^+$, 1.6), 177 (100), 149 (24), 135 (45), 107 (20), 79 (32), 63 (10) | −86.4 |
| IIIAo-2 | 193 (M$^+$—COCH$_3$, 7.6), 191 (15), 149 (100), 135 (13), 121 (14), 107 (19), 79 (23), 43 (12) | −90.2 |
| IIIAo-3 | — | −93.8 |
| IIIAo-4 | — | −96.9 |
| IIIAp-1 | 236 (M$^+$, 1.2), 191 (100), 190 (47), 163 76), 146 (13), 135 (58), 119 (27), 107 (24), 79 (42), 63 (13) | −86.1 |
| IIIAp-2 | 219 (M$^+$—OC$_2$H$_5$, 16), 191 (65), 163 (100), 135 (51), 107 (28), 79 (44), 57 (23), 45 (12) | — |
| IIIAq-1 | 180 (M$^+$, 0.6), 149 (100), 148 (37), 121 (53), 118 (14), 107 (64), 91 (43), 77 (24), 43 (12) | −83.5 |
| IIIAq-2 | 177 (M$^+$—OCH$_3$, 2.8), 165 (15), 149 (47), 148 (15), 135 (100), 107 (90), 93 (29), 77 (24), 63 (13), 43 (30) | −87.8 |
| IIIBa (IIIDa) | 203 (M$^+$—CH$_3$, 24), 175 (32), 173 (25), 157 (16), 129 (20), 103 (12), 75 (100), 73 (96), 55 (33), 45 (15) | 24.1 |
| IIIBb (IIIDb) | 217 (M$^+$—CH$_3$, 34), 189 (31), 187 (40), 171 (24), 161 (37), 159 (20), 143 (13), 142 (24), 129 (44), 117 (39), 116 (20), 114 (29), 97 (31), 75 (75), 73 (100), 72 (20), 58 (16), 55 (71), 45 (24) | 23.6 |
| IIIBc (IIIDc) | 257 (M$^+$—CH$_3$, 26), 229 (11), 227 (14), 183 (21), 154 (23), 117 (13), 110 (13), 81 (37), 80 (14), 75 (61), 73 (100), 45 (12) | 23.6 |
| IIIBd (IIIDd) | 251 (M$^+$—CH$_3$, 26), 223 (31), 149 (14), 103 (16), 75 (100), 73 (23) | — |
| IIIBe (IIIDe) | 201 (M$^+$—CH$_3$, 14), 173 (31), 75 (100), 73 (32), 45 (13) | — |
| IIIBf-1 (IIIDf-1) | 267 (M$^+$—CH$_3$, 46), 205 (79), 167 (100), 153 (24), 151 (55), 137 (22), 123 (26), 121 (38), 105 (93), 91 (53), 59 (23), 55 (33), 45 (16) | — |

TABLE 2-3

| Compound [1] | Fragment peak values of mass spectra, m/z (relative intensity) [2] | $^{29}$Si-NMR (δ, ppm) [3] |
|---|---|---|
| IIIAr-1 (IIICr-1) | 217 (M$^+$—OC$_2$H$_5$, 12), 177 (100), 135 (45), 107 (13), 91 (10), 79 (13), 63 (10) | −45.4 |
| IIIAr-2 (IIICr-2) | 231 (M$^+$—OC$_2$H$_5$, 4.0), 191 (53), 149 (100), 121 (11), 107 (20), 79 (15), 43 (10) | −46.0 |
| IIIAs-1 (IIICs-1) | 254 (M$^+$, 1.2), 209 (38), 177 (100), 176 (27), 167 (25), 149 (13), 139 (34), 135 (39), 132 (14), 123 (12), 107 (11), 79 (15), 45 (13) | −60.0 |
| IIIAs-2 (IIICs-2) | 223 (M$^+$—OC$_2$H$_5$, 14), 191 (79), 181 (37), 167 (12), 149 (100), 139 (58), 121 (19), 107 (17), 79 (15), 45 (13), 43 (16) | −61.9 |
| IIIAt-1 (IIICt-1) | 215 (M$^+$—OCH$_3$, 0.2), 149 (71), 107 (100), 77 (29), 59 (11), 43 (27) | −46.2 |

TABLE 2-3-continued

| Compound [1] | Fragment peak values of mass spectra, m/z (relative intensity) [2] | $^{29}$Si-NMR (δ, ppm) [3] |
|---|---|---|
| IIIAt-2 (IIICt-2) | 232 (M$^+$—COCH$_2$, 2.5), 137 (12), 135 (100), 125 (10), 93 (43), 43 (69) | −47.1 |
| IIIAu-1 (IIICu-1) | 479 (M$^+$—OC$_2$H$_5$, 4.7), 177 (100), 151 (49), 149 (11), 135 (75), 125 (13), 123 (41), 109 (13), 107 (23), 81 (19), 79 (19), 43 (32) | −48.6 |
| IIIAu-2 (IIICu-2) | 496 (M$^+$—COCH$_2$, 0.2), 191 (19), 151 (24), 149 (100), 125 (14), 123 (71), 121 (14), 107 (24), 81 (16), 79 (18), 43 (67) | −48.4 |
| IIIAv-1 (IIICv-1) | 579 (M$^+$—OC$_2$H$_5$, 2.9), 177 (100), 151 (52), 149 (12), 135 (76), 125 (14), 123 (41), 109 (14), 107 (22), 81 (17), 79 (18), 69 (11), 43 (33) | −48.6 |
| IIIAv-2 (IIICv-2) | 191 (M$^+$—C$_6$F$_{17}$C$_2$H$_4$, 21), 151 (27), 119 (100), 125 (14), 123 (67), 121 (13), 107 (21), 81 (12), 79 (15), 43 (60) | −48.4 |
| IIIAw | 153 (M$^+$—CH$_3$, 17), 151 (M$^+$—CH$_3$, 50), 97 (11), 95 (43), 93 (33), 75 (82), 73 (100), 45 (45), 43 (19) | 27.5 |
| IIIAx | 187 (M$^+$—CH$_3$, 2.7), 185 (M$^+$—CH$_3$, 3.7), 95 (26), 93 (73), 75 (12), 73 (100), 45 (31), 43 (15) | 30.9 |
| IIIAy | 221 (M$^+$—CH$_3$, 2.0), 219 (M$^+$—CH$_3$, 2.1), 113 (10), 95 (22), 93 (66), 73 (100), 63 (17), 45 (29), 43 (16) | 33.4 |
| IIIAz | 187 (M$^+$—CH$_3$, 2.8), 121 (15), 95 (10), 93 (29), 77 (86), 73 (100), 63 (19), 45 (26), 4.3 (15) | 33.6 |
| IIIAaa | 284 (M$^+$, 1.3), 269 (100), 195 (37), 167 (29), 159 (11), 125 (45), 117 (20), 77 (69), 75 (27), 73 (10) | 29.2 |
| IIIAab-1 (IIICab-1) | 251 (M$^+$—CH3, 1.0), 249 (M$^+$—CH$_3$, 0.87), 187 (15), 185 (22), 123 (16), 115 (17), 113 (23), 103 (100), 95 (22), 93 (19), 75 (36), 59 (19), 45 (17) | 4.3 |
| IIIAac-1 (IIICac-1) | 311 (M$^+$—CH$_3$, 2.5), 309 (M$^+$—CH$_3$, 2.4), 281 (18), 279 (18), 264 (11), 246 (43), 244 (64), 217 (27), 215 (38), 163 (100), 153 (15), 145 (19), 143 (28), 135 (17), 125 (21), 119 (58), 117 (16), 115 (16), 107 (20), 99 (15), 97 (39), 91 (20), 79 (45), 63 (29), 62 (13), 45 (21), 43 (24) | −87.5 |

1) In cases where the acyloxysilanes correspond to the acyloxysilanes represented by General Formula (IIIC) or (IIID), the compound numbers: IIICs or IIIDs are indicated in parentheses.
2) GC-MS (EI, 70 eV)
3) In CDCl$_3$.

Since, in the production method according to the present invention, a catalyst is used to allow for a more efficient reaction, the reaction proceeds easily even at a low temperature, such as room temperature.

For example, when the reaction of (Ii) with (IIAa) was carried out in the absence of a catalyst, under the conditions of 25° C. or 100° C. for 20 minutes, it was unable to obtain any acyloxysilane at all, as can be seen from the results of Comparative Examples 1 and 2 in Table 1-3. In the method of the present invention using a catalyst, however, it was possible to obtain an acyloxysilane (IIIAo) with a good yield of 81%, even under the stirring conditions of 25° C. for 10 minutes, as can be seen from the results of Example 31.

These results indicate that an acyloxysilane can be produced efficiently even at a low temperature, by using a catalyst in the method of the present invention.

Further, in the present invention, it is possible to selectively convert some or all of a plurality of the alkoxy groups in the starting alkoxysilane to an acyloxy group(s), by selecting the type of catalyst and controlling the reaction conditions.

For example, in the reaction of an alkoxysilane (Id) with the carboxylic anhydride (IIAa), a compound (IIIAi-1) in which one of two methoxy groups in the starting alkoxysilane had been converted to an acetoxy group, and a compound (IIIAi-2) in which both the two methoxy groups had been converted to acetoxy groups were obtained in a ratio of (IIIAi-1):(IIIAi-2) of (≥99:1), by carrying out a reaction using CBV780 as a catalyst under the stirring conditions of 25° C. for five minutes, or using CBV600 as a catalyst under the stirring conditions of 110° C. for five minutes, as can be seen from the results of Examples 20 and 22 in Table 1-1. In other words, it was possible to selectively obtain a compound in which only one of two methoxy groups had been converted to an acetoxy group, in each of these Examples. On the other hand, as can be seen from the results of Example 21, the compound (IIIAi-1) and the compound (IIIAi-2) were obtained in a ratio of (IIIAi-1):(IIIAi-2) of (≤1:99), by carrying out a reaction using CBV780 as a catalyst under the stirring conditions of 110° C. for five minutes. In other words, it was possible to selectively obtain a compound in which both the two methoxy groups had been converted to acetoxy groups.

Further, in the reaction of the alkoxysilane (Ii) with the carboxylic anhydride (IIAa), it was possible to control the amount of acyloxy groups to be introduced, by selecting the type of the catalyst and the like, as can be seen from the results of Examples 67 to 72 in Table 1-3 and Table 1-4. In cases where ruthenium (III) chloride was used as a catalyst, a compound (IIIAo-2) in which two ethoxy groups in the starting alkoxysilane had been converted to acetoxy groups was obtained as a major product (Example 67). In cases where aluminum (III) trifluoromethanesulfonate or trifluoromethanesulfonic acid was used as catalyst, a compound (IIIAo-3) in which three ethoxy groups in the starting alkoxysilane had been converted to acetoxy groups was obtained as a major product (Examples 68 and 72). In cases where iron (III) perchlorate, scandium (III) bis(trifluoromethanesulfonyl)imide, or indium (III) bis(trifluoromethanesulfonyl)imide was used as a catalyst, a compound (IIIAo-4) in which four ethoxy groups in the starting alkoxysilane had been converted to acetoxy groups was obtained as a major product (Examples 69 to 71). Further, in cases where acetonitrile was used as a solvent in the reaction using iron (III) perchlorate as a catalyst, it was possible to selectively obtain a compound (IIIAo-2) in which two ethoxy groups in the starting alkoxysilane had been converted to acetoxy groups (Example 72).

These results indicate that, it is possible to selectively convert some or all of the plurality of alkoxy groups in the starting alkoxysilane to an acyloxy group(s), by properly controlling and selecting the reaction conditions, such as the reaction temperature, the type of catalyst and solvent, and the like.

Further, in the production method according to the present invention, the reaction can be accelerated by heating using microwave irradiation.

For example, in the reaction of the alkoxysilane (Ia) with a carboxylic anhydride (IIAc), the yield of the resulting acyloxysilane (IIIAc) in the case of carrying out the reaction using a microwave irradiation apparatus, under the reaction conditions of stirring at 60° C. for five minutes, or at 80° C. for five minutes, was 41% or 81%, respectively, as can be seen from the results of Examples 48 and 50 in Table 1-2. On the other hand, as can be seen from the results of Examples 49 and 51, in cases where the reaction was carried out using an oil bath heating device instead of the microwave irradiation apparatus, at the same reaction temperature and for the same reaction time as Example 48 or 50, the yield of the acyloxysilane (IIIAc) was 36% or 73%, respectively.

Further, in the reaction of the alkoxysilane (Ia) with a carboxylic anhydride (IIBa), as can be seen from the results of Examples 52 and 54 in Table 1-3, the yield of the resulting acyloxysilane (IIIBa) in the case of carrying out the reaction using a microwave irradiation apparatus, under the reaction conditions of stirring at 120° C. for five minutes, or for 15 minutes, was 42% or 70%, respectively. In contrast, as can be seen from the results of Examples 53 and 55, in cases where the reaction was carried out using an oil bath heating device instead of the microwave irradiation apparatus, at the same reaction temperature and for the same reaction time as Example 52 or 54, the yield of the acyloxysilane (IIIBa) was 32% or 65%, respectively.

These results indicate that, in the production method according to the present invention, although the reaction can be carried out sufficiently efficiently by using a common heating technique such as heating with an oil bath or the like, the use of microwave heating allows for a more efficient reaction.

Each of the acyloxysilanes obtained by the above describe production methods can be easily isolated and purified, by separating the catalyst by centrifugal separation, filtration or the like, followed by operations such as distillation and recrystallization, as will be described in the following Examples.

Example 86

A mixture of 4.8 mmol of (ethoxy)dimethyl(phenyl)silane (Ib), 19.3 mmol of acetic anhydride (IIAa) and 15 mg of CBV780 (manufactured by Zeolyst International) was introduced into a reaction tube. The reaction tube was then sealed, followed by stirring at 110° C. for 10 minutes, using a microwave irradiation apparatus (Initiator; manufactured by Biotage AB). After separating the catalyst solids by centrifugation, and separating the supernatant, the catalyst was washed with toluene (once, with 1 mL). Then the separated supernatant was combined with the washing liquid, and the resulting solution was concentrated under reduced pressure, and distilled in a short path distillation apparatus. As a result, 3.26 mmol (yield: 68%) of (acetoxy)dimethyl(phenyl)silane (IIIAg) was obtained.

The physical property values, spectral data, and the like of the resulting compound (IIIAg) were as follows.

Boiling point: from 95 to 100° C./3 mmHg (distillation temperature in short path distillation)

IR (liquid film): 1722, 1429, 1370, 1251, 1122, 1018, 936, 840, 821, 796, 733, 698, 471, 407 cm$^{-1}$ $^1$H-NMR (CDCl$_3$): δ 0.58 (s, 6H, SiCH$_3$), 2.09 (s, 3H, CH$_3$CO), 7.38-7.45 and 7.63-7.66 (each m, 5H, C$_6$H$_5$)

$^{13}$C-NMR (CDCl$_3$): δ -1.7, 22.8, 127.9, 130.1, 133.6, 135.6, 171.6

$^{29}$Si-NMR (CDCl$_3$): δ 11.7

Example 87

A mixture of 4.0 mmol of (ethoxy)methyldi(phenyl)silane (Ic), 16.1 mmol of acetic anhydride (IIAa) and 50 mg of CBV 780 (manufactured by Zeolyst International) was introduced into a reaction tube. The reaction tube was then sealed, followed by stirring at 110° C. for 10 minutes, using a microwave irradiation apparatus (Initiator; manufactured by Biotage AB). The post-treatment and the distillation were carried out in the same manner as in Example 86, to obtain 3.24 mmol (yield 81%) of (acetoxy)methyldi(phenyl)silane (IIIAh).

The physical property values and the spectral data of the resulting compound (IIIAh) were as follows.

Boiling point: from 135 to 140° C./1 mmHg (distillation temperature in short path distillation)

IR (liquid film): 1726, 1429, 1369, 1247, 1122, 1018, 935, 797, 767, 737, 698, 476, 445 cm$^{-1}$ $^1$H-NMR (CDCl$_3$): δ 0.88 (s, 3H, SiCH$_3$), 2.16 (s, 3H, CH$_3$CO), 7.38-7.47 and 7.63-7.66 (each m, 10H, C$_6$H$_5$)

$^{13}$C-NMR (CDCl$_3$): δ -2.7, 22.9, 127.9, 130.3, 133.9, 134.5, 171.4

$^{29}$Si-NMR (CDCl$_3$): δ 0.3

Example 88

A mixture of 5.0 mmol of methyldi(methoxy)(phenyl)silane (Id), 7.5 mmol of acetic anhydride (IIAa) and 15 mg of CBV780 (manufactured by Zeolyst International) was introduced into a reaction tube. The reaction tube was then sealed, followed by stirring at room temperature (25° C.) for seven minutes. The post-treatment and the distillation were carried out in the same manner as in Example 86, to obtain 3.25 mmol (yield: 65%) of (acetoxy)methyl(methoxy)(phenyl)silane (IIIAi-1).

The physical property values and the spectral data of the resulting compound (IIIAi-1) were as follows.

Boiling point: from 95 to 105° C./3.5 mmHg (distillation temperature in short path distillation)

IR (liquid film): 1729, 1430, 1371, 1250, 1192, 1124, 1092, 1019, 938, 829, 798, 777, 740, 699, 476, 431 cm$^{-1}$ $^1$H-NMR (CDCl$_3$): δ 0.58 (s, 3H, SiCH$_3$), 2.15 (s, 3H, CH$_3$CO), 3.64 (s, 3H. CH$_3$O), 7.38-7.47 and 7.64-7.68 (each m, 5H, C$_6$H$_5$)

$^{13}$C-NMR (CDCl$_3$): δ -4.0, 22.7, 51.6, 128.0, 130.7, 132.5, 133.8, 171.0

$^{29}$Si-NMR (CDCl$_3$): δ -14.0

Example 89

A mixture of 3.3 mmol of methyldi(methoxy)(phenyl)silane (Id), 13.2 mmol of acetic anhydride (IIAa) and 10 mg of CBV780 (manufactured by Zeolyst International) was introduced into a reaction tube. The reaction tube was then sealed, followed by stirring at 110° C. for five minutes using a microwave irradiation apparatus (Initiator; manufactured by Biotage AB). The post-treatment and the distillation were carried out in the same manner as in Example 86, to obtain 2.67 mmol (yield: 81%) of di(acetoxy)methyl(phenyl)silane (IIIAi-2).

The physical property values and the spectral data of the resulting compound (IIIAi-2) were as follows.

Boiling point: from 95 to 105° C./0.9 mmHg (distillation temperature in short path distillation)

IR (liquid film): 1736, 1431, 1371, 1237, 1125, 1018, 940, 801, 741, 698, 597, 474, 432 cm$^{-1}$ $^1$H-NMR (CDCl$_3$): δ 0.82 (s, 3H, SiCH$_3$), 2.14 (s, 6H, CH$_3$CO), 7.39-7.50 and 7.70-7.73 (each m, 5H, C$_6$H$_5$)

$^{13}$C-NMR (CDCl$_3$): δ −3.0, 22.6, 128.0, 130.9, 131.3, 133.9, 170.6

$^{29}$Si-NMR (CDCl$_3$): δ −11.7

Example 90

A mixture of 7.5 mmol of methyldi(methoxy)(phenyl)silane (Id), 11.3 mmol of propionic anhydride (IIAb) and 45 mg of CBV780 (manufactured by Zeolyst International) was introduced into a reaction tube. The reaction tube was then sealed, followed by stirring at room temperature (25° C.) for 15 minutes. The post-treatment and the distillation were carried out in the same manner as in Example 86, to obtain 5.78 mmol (yield: 77%) of methyl(methoxy)(phenyl)(propanoyloxy)silane (IIIAj-1).

The physical property values and the spectral data of the resulting compound (IIIAj-1) were as follows.

Boiling point: from 100 to 105° C./4 mmHg (distillation temperature in short path distillation)

IR (liquid film): 1727, 1430, 1361, 1261, 1189, 1124, 1084, 997, 892, 829, 799, 741, 699, 478, 441 cm$^{-1}$ $^1$H-NMR (CDCl$_3$): δ 0.58 (s, 3H, SiCH$_3$), 1.15 (t, J=7.5 Hz, 3H, CH$_3$CCO), 2.429 and 2.430 (each q, each J=7.5 Hz, 2H, CH$_2$CO), 3.64 (s, 3H. CH$_3$O), 7.38-7.47 and 7.64-7.68 (each m, 5H, C$_6$H$_5$)

$^{13}$C-NMR (CDCl$_3$): δ −4.0, 9.1, 29.0, 51.5, 128.0, 130.7, 132.6, 133.8, 174.3

$^{29}$Si-NMR (CDCl$_3$): δ −14.0

Example 91

A mixture of 5.0 mmol of methyldi(methoxy)(phenyl)silane (Id), 14.9 mmol of propionic anhydride (IIAb) and 30 mg of CBV780 (manufactured by Zeolyst International) was introduced into a reaction tube. The reaction tube was then sealed, followed by stirring at 110° C. for 30 minutes using a microwave irradiation apparatus (Initiator; manufactured by Biotage AB). The post-treatment and the distillation were carried out in the same manner as in Example 86, to obtain 4.05 mmol (yield: 81%) of methyl(phenyl)di(propanoyloxy)silane (IIIAj-2).

The physical property values and the spectral data of the resulting compound (IIIAj-2) were as follows.

Boiling point: from 120 to 130° C./2.5 mmHg (distillation temperature in short path distillation)

IR (liquid film): 1735, 1463, 1430, 1360, 1263, 1172, 1125, 1082, 997, 897, 809, 741, 698, 476, 439 cm$^{-1}$ $^1$H-NMR (CDCl$_3$): δ 0.82 (s, 3H, SiCH$_3$), 1.13 (t, J=7.5 Hz, 3H, CH$_3$CCO), 2.429 and 2.433 (each q, each J=7.5 Hz, 2H, CH$_2$CO), 7.39-7.50 and 7.70-7.74 (each m, 5H, C$_6$H$_5$)

$^{13}$C-NMR (CDCl$_3$): δ −2.9, 8.9, 28.9, 128.0, 131.18, 131.25, 133.9, 173.9

$^{29}$Si-NMR (CDCl$_3$): δ −12.0

Example 92

A mixture of 4.9 mmol of tri(methoxy)(phenyl)silane (If), 7.3 mmol of acetic anhydride (IIAa) and 30 mg of CBV780 (manufactured by Zeolyst International) was introduced into a reaction tube. The reaction tube was then sealed, followed by stirring at room temperature (25° C.) for 30 minutes. The post-treatment and the distillation were carried out in the same manner as in Example 86, to obtain 2.45 mmol (yield: 50%) of (acetoxy)di(methoxy)(phenyl)silane (IIIAl-1).

The physical property values and the spectral data of the resulting compound (IIIAl-1) were as follows.

Boiling point: from 120 to 130° C./2.5 mmHg (distillation temperature in short path distillation)

IR (liquid film): 1741, 1431, 1372, 1253, 1193, 1132, 1095, 1020, 942, 826, 778, 742, 700, 483 cm$^{-1}$ $^1$H-NMR (CDCl$_3$): δ 2.15 (s, 3H, CH$_3$CO), 3.70 (s, 6H, CH$_3$O), 7.38-7.50 and 7.70-7.73 (each m, 5H, C$_6$H$_5$)

$^{13}$C-NMR (CDCl$_3$): δ 22.5, 51.6, 128.03, 128.05, 131.2, 134.8, 170.0

$^{29}$Si-NMR (CDCl$_3$): δ −57.4

Example 93

A mixture of 4.9 mmol of tri(methoxy)(phenyl)silane (If), 19.4 mmol of acetic anhydride (IIAa) and 60 mg of CBV780 (manufactured by Zeolyst International) was introduced into a reaction tube. The reaction tube was then sealed, followed by stirring at 50° C. for 20 minutes using a microwave irradiation apparatus (Initiator; manufactured by Biotage AB). The post-treatment and the distillation were carried out in the same manner as in Example 86, to obtain 2.45 mmol (yield: 50%) of di(acetoxy)(methoxy)(phenyl)silane (IIIAl-2).

The physical property values and the spectral data of the resulting compound (IIIAl-2) were as follows.

Boiling point: from 115 to 120° C./1 mmHg (distillation temperature in short path distillation)

$^1$H-NMR (CDCl$_3$): δ 2.17 (s, 6H, CH$_3$CO), 3.80 (s, 3H, CH$_3$O), 7.40-7.52 and 7.76-7.79 (each m, 5H, C$_6$H$_5$)

$^{13}$C-NMR (CDCl$_3$): δ 22.4, 52.5, 126.8, 128.0, 131.7, 134.9, 169.6

$^{29}$Si-NMR (CDCl$_3$): δ −60.3

Example 94

A mixture of 7.5 mmol of tetra(ethoxy)silane (Ii), 11.3 mmol of propionic anhydride (IIAb) and 45 mg of CBV780 (manufactured by Zeolyst International) was introduced into a reaction tube. The reaction tube was then sealed, followed by stirring at room temperature (25° C.) for 15 minutes. The post-treatment and the distillation were carried out in the same manner as in Example 86, to obtain 6.75 mmol (yield: 90%) of tri(ethoxy)(propanoyloxy)silane (IIIAp-1).

The physical property values and the spectral data of the resulting compound (IIIAp-1) were as follows.

Boiling point: from 80 to 90° C./9 mmHg (distillation temperature in short path distillation)

IR (liquid film): 1739, 1392, 1362, 1279, 1205, 1169, 1107, 1085, 1002, 972, 898, 797, 471 cm$^{-1}$ $^1$H-NMR (CDCl$_3$): δ 1.14 (t, J=7.5 Hz, 3H, CH$_3$CCO), 1.25 (t, J=7.0 Hz, 9H, CH$_3$CO, 2.41 (q, J=7.5 Hz, 2H, CH$_2$CO), 3.93 (q, J=7.0 Hz, 6H, CH$_2$O)

$^{13}$C-NMR (CDCl$_3$): δ 9.0, 17.9, 28.8, 59.9, 173.0
$^{29}$Si-NMR (CDCl$_3$): δ −86.1

Example 95

A mixture of 3.2 mmol of (ethoxy)trimethylsilane (Ia), 2.6 mmol of succinic anhydride (IIBa), 20 mg of CBV780 manufactured by Zeolyst International) and 4 mL of 1,2-dichlorobenzene was introduced into a reaction tube. The reaction tube was then sealed, followed by stirring at 120° C. for 60 minutes using a microwave irradiation apparatus (Initiator; manufactured by Biotage AB). The post-treatment and the distillation were carried out in the same manner as in Example 86, to obtain 1.56 mmol of (yield: 60%) of [(3-ethoxycarbonyl)propanoyloxy]trimethylsilane (IIIBa).

The physical property values and the spectral data of the resulting compound (IIIBa) were as follows.

Boiling point: from 90 to 100° C./2.5 mmHg (distillation temperature in short path distillation)
IR (liquid film): 1738, 1720, 1415, 1372, 1351, 1322, 1254, 1213, 1166, 1025, 890, 852, 764, 736 cm$^{-1}$
$^1$H-NMR (CDCl$_3$): δ 0.28 (s, 9H, SiCH$_3$), 1.26 (t, J=7.2 Hz, 3H, CCH$_3$), 2.56-2.65 (m, 4H, CH$_2$CH$_2$), 4.15 (q, J=7.2 Hz, 2H, OCH$_2$)
$^{13}$C-NMR (CDCl$_3$): δ −0.3, 14.2, 29.4, 30.7, 60.6, 172.4, 172.7
$^{29}$Si-NMR (CDCl$_3$): δ 24.1

Example 96

A mixture of 3.4 mmol of (ethoxy)trimethylsilane (Ia), 2.6 mmol of glutaric anhydride (IIBb), 20 mg of CBV780 (manufactured by Zeolyst International) and 4 mL of 1,2-dichlorobenzene was introduced into a reaction tube. The reaction tube was then sealed, followed by stirring at 120° C. for 60 minutes using a microwave irradiation apparatus (Initiator; manufactured by Biotage AB). The post-treatment and the distillation were carried out in the same manner as in Example 86, to obtain 1.61 mmol (yield: 62%) of (3-ethoxycarbonyl)propanoyloxy]trimethylsilane (IIIBb).

The physical property values and the spectral data of the resulting compound (IIIBb) were as follows.

Boiling point: from 85 to 95° C./1.8 mmHg (distillation temperature in short path distillation)
IR (liquid film): 1737, 1717, 1419, 1375, 1318, 1254, 1198, 1155, 1030, 906, 851, 764 cm$^{-1}$
$^1$H-NMR (CDCl$_3$): δ 0.28 (s, 9H, SiCH$_3$), 1.26 (t, J=7.2 Hz, 3H, CCH$_3$), 1.92 (quint, J=7.5 Hz, 2H, CH$_2$CCO), 2.36 and 2.37 (each t, J=7.5 Hz, each 2H, CH$_2$CO), 4.13 (q, J=7.2 Hz, 2H, OCH$_2$)
$^{13}$C-NMR (CDCl$_3$): δ −0.3, 14.2, 20.2, 33.3, 34.9, 60.3, 173.0, 173.5
$^{29}$Si-NMR (CDCl$_3$): δ 23.6

Example 97

A mixture of 3.2 mmol of (ethoxy)trimethylsilane (Ia), 2.6 mmol of cyclohexane-1,2-dicarboxylic anhydride (IIBc), 60 mg of CBV780 (manufactured by Zeolyst International) and 2 mL of 1,2-dichlorobenzene was introduced into a reaction tube. The reaction tube was then sealed, followed by stirring at 90° C. for 45 minutes using a microwave irradiation apparatus (Initiator; manufactured by Biotage AB). The post-treatment and the distillation were carried out in the same manner as in Example 86, to obtain 1.56 mmol (yield: 60%) of (2-ethoxycarbonyl)cyclohexanylcarbonyloxy]trimethylsilane (IIIBc).

The physical property values and the spectral data of the resulting compound (IIIBc) were as follows.

Boiling point: from 125 to 130° C./5 mmHg (distillation temperature in short path distillation)
$^1$H-NMR (CDCl$_3$): δ 0.25 (s, 9H, SiCH$_3$), 1.22 (t, J=7.2 Hz, 3H, CCH$_3$), 1.32-1.55, 1.67-1.80, and 1.90-2.03 (each m, each 2H, (CH$_2$)$_4$), 2.70-2.85 (m, 2H, CHCH), 4.07-4.17 (m, 2H, OCH$_2$)
$^{13}$C-NMR (CDCl$_3$): δ −0.4, 14.2, 23.7, 23.9, 26.2, 26.5, 42.7, 43.7, 60.2, 173.7, 174.2
$^{29}$Si-NMR (CDCl$_3$): δ 23.6

Each of the acyloxysilanes obtained in the above described methods can be used as a surface treatment agent for treating a solid material, such as glass. Specifically, the surface treatment can be carried out, as will be described in the following Examples, by a method in which: an alkoxysilane is reacted with a carboxylic anhydride to obtain an acyloxysilane; a composition containing the resulting acyloxysilane is diluted in an adequate solvent; and a solid material is immersed in the resulting diluted solution.

Example 98

A mixture of 2.0 mmol of tri(ethoxy)(phenyl)silane (II), 2.2 mmol of an acetic anhydride (IIAa) and 10 mg of CBV780 (manufactured by Zeolyst International) was introduced into a reaction tube. The reaction tube was then sealed, followed by stirring at room temperature (25° C.) for 20 minutes. The catalyst solids were separated by centrifugation, and the supernatant was analyzed by gas chromatography or nuclear magnetic resonance spectroscopy. As a result, it was confirmed that 1.7 mmol (yield: 84%) of an acyloxysilane ((acetoxy)di(ethoxy)(phenyl)silane (IIIAs-1) and di(acetoxy)(ethoxy)(phenyl)silane (IIIAs-2); the ratio of (IIIAs-1):(IIIAs-2)=83:17) had been generated.

A quantity of 0.04 mL of the supernatant containing the thus obtained acyloxysilane was dissolved in 0.96 mL of toluene, to prepare a solution for use in surface treatment. A glass plate (1.8×1.8 cm) was immersed in the thus prepared solution at room temperature for two minutes. Subsequently, the glass plate was washed with 3 mL of toluene and 3 mL of acetone, sequentially, and dried at 80° C. for five minutes. The contact angle of the glass plate with respect to water was measured by a contact angle meter (Automatic Contact Angle Meter, DMe-201; manufactured by Kyowa Interface Science Co., LTD.). As a result, it was confirmed that the contact angle changed from 20° in the untreated state to 71° in the treated state. This indicates the fact that the surface of the glass plate has been modified by the acyloxysilane, to obtain an improved water repellency (Table 3).

TABLE 3

| Example [1] | I [2] | II [2] | Temp. (° C.) | Time (min) | III [2] | Yield [3] | Surface treatment liquid [4] | Contact angle [5] |
|---|---|---|---|---|---|---|---|---|
| Example 98 | II | IIAa | 25 | 20 | IIIAs (83:17:0) | 84 | 0.04/0.96 | 71 |

TABLE 3-continued

| Example [1)] [2)] | I [2)] | II [2)] | Temp. (° C.) | Time (min) | III [2)] | Yield [3)] | Surface treatment liquid [4)] | Contact angle [5)] |
|---|---|---|---|---|---|---|---|---|
| Reference Example 1 | II | — | — | — | — | — | 0.04/0.96 | 23 |
| Example 99 | Id | IIAa | 25 | 20 | IIIAi (77:23) | 88 | 0.03/0.97 | 85 |
| Example 100 | Ik | IIAa | 25 | 20 | IIIAr (94:6:0) | 88 | 0.04/0.96 | 81 |
| Example 101 | Im | IIAa | 25 | 20 | IIIAt (76:24:0) | 87 | 0.03/0.97 | 84 |
| Example 102 | In | IIAa | 90 | 15 | IIIAu (72:28:0) | 89 | 0.04/0.96 | 105 |
| Example 103 | Io | IIAa | 90 | 15 | IIIAv (72:28:0) | 88 | 0.05/0.95 | 112 |
| Example 104 | Ii | IIAa | 25 | 20 | IIIAo (80:20:0:0) | 80 | 0.03/0.97 | 77 |
| Example 105 | Ij | IIAa | 60 | 5 | IIIAq (85:15:0:0) | 75 | 0.03/0.97 | 73 |

1) Reaction conditions: I: 2.0 mmol, IIAa: 2.2 mmol, CBV780: 10 mg (in Examples 98, 99, 100, 104, and 105); I: 1.0 mmol, IIAa: 1.1 mmol, CBV780: 10 mg (in Examples 101, 102, and 103).

2) The compound names of Is, IIs, and IIIs are the same as those described in the footnotes of Tables 1.

3) The yield as analyzed by gas chromatography or nuclear magnetic resonance spectroscopy.

4) Prepared by diluting the reaction liquid with toluene. The numbers in each of the Examples indicate: the amount of reaction liquid (mL)/the amount of toluene (mL).

5) The contact angle of the glass plate surface with respect to water, measured by: immersing the glass plate in the surface treatment liquid at room temperature for two minutes, washing the glass plate with toluene and acetone, drying the glass plate at 80° C., then dropping water on the glass plate, and measuring the contact angle using a contact angle meter (Automatic Contact Angle Meter, DMc-201; manufactured by Kyowa Interface Science Co., LTD.).

Reference Example 1

A quantity of 0.04 ml of tri(ethoxy)(phenyl)silane (II) was dissolved in 0.96 mL of toluene, to prepare a solution for use in surface treatment. A glass plate (1.8×1.8 cm) was immersed in the thus prepared solution at room temperature for two minutes, followed by washing and drying, and then the contact angle of the surface of the glass plate with respect to water was measured, in the same manner as in Example 98. As a result, the contact angle was 23°, which was almost the same as 20° in the untreated state. This indicates the fact that, different from the case in which the surface treatment was carried out using the solution containing the acetoxysilane obtained in Example 98, the surface of the glass plate was barely modified under the same treatment conditions, because the solution prepared in this Example had a low reactivity with the solid material surface due to using the starting alkoxysilane as it is (Table 3).

Examples 99 to 105

The same procedure as in Example 98 was repeated with varying reaction conditions (such as starting materials, reaction temperature, reaction time, and the like), to carry out reactions of alkoxysilanes and the analyses of the resulting products. The surface treatment of a glass plate was carried out using each of the resulting acyloxysilanes, and the results are shown in Table 3.

The results of the Examples 98 to 105 indicate that it is possible to carry out the surface treatment of a glass plate, by using a composition containing an acyloxysilane obtained by the method according to the present invention, and by a simple method which only requires immersing a glass plate in a solution containing the composition at room temperature for a short period of time. At the same time, the results also indicate that the contact angle of the surface of the glass plate with respect to water can be controlled within the range of from 71 to 112°, which is an improvement as compared to 20° in the untreated state.

INDUSTRIAL APPLICABILITY

According to the production method of the present invention, it is possible to more efficiently and safely produce an acyloxysilane which is useful as a functional chemical, as well as to provide a novel acyloxysilane obtained thereby, and the use thereof. Therefore, the present invention has a high utility value and a great industrial significance.

What is claimed is:

1. A method for producing an acyloxysilane, comprising a reaction step of reacting an alkoxysilane with a carboxylic anhydride in the presence of a catalyst, wherein
the alkoxysilane is an alkoxysilane represented by the following General Formula (I), $$R^1_p R^2_q R^3_r Si(OR^4)_{4-(p+q+r)} \quad (I)$$

wherein p, q, r, and the sum of p+q+r are each an integer of 0 or more and 3 or less; each of $R^1$, $R^2$ and $R^3$ independently represents a hydrocarbon group having from 1 to 24 carbon atoms or a hydrogen atom; $R^4$(s) is/are an alkyl group(s) having from 1 to 6 carbon atoms; and in cases where each of $R^1$, $R^2$, and $R^3$ is a hydrocarbon group, some of the hydrogen atoms of the hydrocarbon group is/are optionally substituted with a group(s) not participating in the reaction;
the carboxylic anhydride is a carboxylic anhydride represented by the following General Formula (IIA) or (IIB), $$(R^5CO)_2O \quad (IIA)$$

wherein each $R^5$ is a hydrocarbon group having from 1 to 24 carbon atoms, and some of the hydrogen atoms of the hydrocarbon group is/are optionally substituted with a group(s) not participating in the reaction;

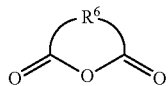
(IIB)

wherein R⁶ is a divalent hydrocarbon group having from 2 to 24 carbon atoms, and some of the hydrogen atoms of the hydrocarbon group is/are optionally substituted with a group(s) not participating in the reaction;
the catalyst is an acid catalyst;
wherein the acid catalyst is (i), (ii), or (iii) below:
(i) a zeolite;
(ii) a chloride, a bromide, or a perchlorate containing an element selected from the group consisting of iron, ruthenium, aluminum, scandium, tin, and indium; and
(iii) trifluoromethanesulfonic acid, pentafluoroethanesulfonic acid, nonafluorobutanesulfonic acid, methanesulfonic acid, a sulfonylimide, or a salt formed from any one of these sulfonic acids and sulfonylimide and an element selected from the group consisting of iron, ruthenium, aluminum, scandium, tin, and indium, and
an acyloxysilane obtained in the reaction step is an acyloxysilane represented by the following General Formula (IIIA) or (IIIB):

(IIIA)

wherein p, q, r, R¹, R², R³, R⁴ and R⁵ are each the same as defined above; and s is an integer equal to or greater than 1 and equal to or less than 4-(p+q+r);

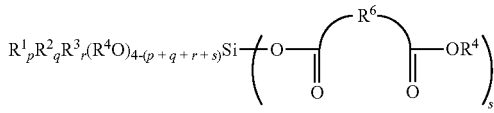
(IIIB)

wherein p, q, r, R¹, R², R³, R⁴ and R⁶ are each the same as defined above; and s is an integer equal to or greater than 1 and equal to or less than 4-(p+q+r).

2. The method for producing an acyloxysilane according to claim 1, wherein the acid catalyst is a zeolite, and the zeolite has a silica/alumina ratio (amount of substance ratio) of from 3 to 1,000.

3. The method for producing an acyloxysilane according to claim 1, wherein the acid catalyst is a zeolite, and the zeolite is at least one selected from the group consisting of USY-type zeolites, beta-type zeolites, Y-type zeolites, ZSM-5-type zeolites, and mordenite-type zeolites.

4. The method for producing an acyloxysilane according to claim 1, wherein the acid catalyst is a zeolite, and the zeolite is at least one selected from the group consisting of USY-type zeolites, beta-type zeolites, Y-type zeolites, ZSM-5-type zeolites, and mordenite-type zeolites.

5. The method for producing an acyloxysilane according to claim 1, wherein the acid catalyst is a chloride, a bromide, or a perchlorate containing an element selected from the group consisting of iron, ruthenium, tin, and indium.

6. The method for producing an acyloxysilane according to claim 1, wherein the acid catalyst is iron (Ill) chloride, iron (III) bromide, iron (III) perchlorate, ruthenium (III) chloride, indium (Ill) chloride, or tin (IV) chloride.

7. The method for producing an acyloxysilane according to claim 1, wherein the acid catalyst is trifluoromethanesulfonic acid, bis(trifluoromethanesulfonyl)imide, or a salt formed from one of trifluoromethanesulfonic acid and bis(trifluoromethanesulfonyl)imide and an element selected from the group consisting of iron, ruthenium, aluminum, scandium, tin, and indium.

8. The method for producing an acyloxysilane according to claim 1, wherein the acid catalyst is trifluoromethanesulfonic acid, bis(trifluoromethanesulfonyl)imide, or a salt formed from one of trifluoromethanesulfonic acid and bis(trifluoromethanesulfonyl)imide and an element selected from the group consisting of iron, aluminum, scandium, and indium.

9. The method for producing an acyloxysilane according to claim 1, wherein the acid catalyst is trifluoromethanesulfonic acid, bis(trifluoromethanesulfonyl)imide, aluminum (III) trifluoromethanesulfonate, iron(III) trifluoromethanesulfonate, scandium(III) bis(trifluoromethanesulfonyl)imide, or indium (III) bis(trifluoromethanesulfonyl)imide.

* * * * *

UNITED STATES PATENT AND TRADEMARK OFFICE
CERTIFICATE OF CORRECTION

PATENT NO. : 10,316,046 B2
APPLICATION NO. : 15/556808
DATED : June 11, 2019
INVENTOR(S) : Hiroshi Yamashita et al.

It is certified that error appears in the above-identified patent and that said Letters Patent is hereby corrected as shown below:

In the Claims

At Column 38, Line 20, "iron (Ill)" should read -- iron (III) --.

At Column 38, Line 22, "indium (Ill)" should read -- indium (III) --.

Signed and Sealed this
Seventeenth Day of March, 2020

Andrei Iancu
*Director of the United States Patent and Trademark Office*